(12) United States Patent
Xie et al.

(10) Patent No.: US 11,918,620 B2
(45) Date of Patent: Mar. 5, 2024

(54) TRADITIONAL CHINESE MEDICINE COMPOSITION, AND PREPARATION METHOD THEREFOR AND APPLICATION THEREOF

(71) Applicant: Suzhou Regen-PharmaTech Co., Ltd., Jiangsu (CN)

(72) Inventors: Be Xie, Beijing (CN); Xuefeng Ren, Beijing (CN)

(73) Assignee: Suzhou Regen-PharmaTech Co., Ltd., Suzhou (CN)

( * ) Notice: Subject to any disclaimer, the term of this patent is extended or adjusted under 35 U.S.C. 154(b) by 0 days.

(21) Appl. No.: 17/802,380

(22) PCT Filed: Jan. 20, 2021

(86) PCT No.: PCT/CN2021/072897
§ 371 (c)(1),
(2) Date: Aug. 25, 2022

(87) PCT Pub. No.: WO2021/169682
PCT Pub. Date: Sep. 2, 2021

(65) Prior Publication Data
US 2023/0121249 A1    Apr. 20, 2023

(30) Foreign Application Priority Data
Feb. 26, 2020   (CN) .......................... 202010121966.6

(51) Int. Cl.
| | | |
|---|---|---|
| *A61K 36/9068* | (2006.01) | |
| *A61K 35/618* | (2015.01) | |
| *A61K 35/62* | (2006.01) | |
| *A61K 36/062* | (2006.01) | |
| *A61K 36/233* | (2006.01) | |
| *A61K 36/284* | (2006.01) | |
| *A61K 36/344* | (2006.01) | |
| *A61K 36/484* | (2006.01) | |
| *A61K 36/54* | (2006.01) | |
| *A61K 36/65* | (2006.01) | |
| *A61K 36/69* | (2006.01) | |
| *A61K 36/752* | (2006.01) | |
| *A61K 36/8888* | (2006.01) | |
| *A61K 36/899* | (2006.01) | |
| *A61P 3/06* | (2006.01) | |
| *A61P 9/10* | (2006.01) | |

(52) U.S. Cl.
CPC ........ *A61K 36/9068* (2013.01); *A61K 35/618* (2013.01); *A61K 35/62* (2013.01); *A61K 36/062* (2013.01); *A61K 36/233* (2013.01); *A61K 36/284* (2013.01); *A61K 36/344* (2013.01); *A61K 36/484* (2013.01); *A61K 36/54* (2013.01); *A61K 36/65* (2013.01); *A61K 36/69* (2013.01); *A61K 36/752* (2013.01); *A61K 36/8888* (2013.01); *A61K 36/899* (2013.01); *A61P 3/06* (2018.01); *A61P 9/10* (2018.01)

(58) Field of Classification Search
None
See application file for complete search history.

(56) References Cited

FOREIGN PATENT DOCUMENTS

| CN | 101548997 A | 10/2009 |
|---|---|---|
| CN | 102671128 A | 9/2012 |
| KR | 20160057819 A | 5/2016 |

OTHER PUBLICATIONS

Duan, et al., World J. Gastroenterol., 23:7242. (Year: 2017).*
CN100421725C English translation from Google Patents. (Year: 2008).*
Zhou, et al., J. Trad. Chinese Med. Sci., 5:390. (Year: 2018).*
International Search Report dated Mar. 26, 2021, in corresponding to International Application No. PCT/CN2021/072897; 8 pages (with English Translation).
Zheng, Xian et al., "Effect of Dachaihu Decoction on the Lipid Metabolism and Inflammatory Factor ExpressiOn in Atherosclerotic Rabbits", Journal of Traditional Chinese Medicine, vol. 54, No. 19, Oct. 2, 2013 (Oct. 2, 2013), ISSN: 1001-1668, 5 pgs.
Zhang, Lifen, "Dyslipidemia"Non official translation: Research and Application on Synopsis of Golden Chamber, Aug. 31, 2008 (Aug. 31, 2008), 7 pgs.
Yin, Xiang-jun et al., "Nine methods for syndrome differentiation of dyslipidemia from ancient prescription", China Journal of Traditional Chinese Medicine and Pharmacy, vol. 31, No. 6, Jun. 1, 2016 (Jun. 1, 2016), ISSN: 1673-1727, 3 pgs.
Hu, Qingyi et al., "Non-official translation: Clinical Observation of Dachaihu Decoction on Lowering Blood Lipid", Shandong Journal of Traditional Chinese Medicine, vol. 14, No. 01, Jan. 20, 1995 (Jan. 20, 1995), 1 pg.
Song, Xiaoxue, et al., "Pharmacological Effect and Clinical Application of Dachaihu Decoction", Acta Chinese Medicine and Pharmacology, vol. 47, No. 4, Jul. 24, 2019 (Jul. 24, 2019), ISSN: 1002-2392, 5 pgs.

(Continued)

*Primary Examiner* — Michael Barker
(74) *Attorney, Agent, or Firm* — Maier & Maier, PLLC

(57) ABSTRACT

A traditional Chinese medicine composition, and preparation method, and application thereof. The traditional Chinese medicine composition includes the following raw medicines in parts by weight: 10-35 parts of root of Chinese thorowax, 5-25 parts of immature bitter orange, 3-20 parts of fresh root and rhizome of sorrel rhubarb, 3-20 parts of root of baikal skullcap, 3-20 parts of white peony root, 3-15 parts of dried ginger, 5-20 parts of leech, 3-20 parts of root of ural licorice, 3-20 parts of root pilose asiabell, 3-20 parts of rhizome of largehead *atractylodes*, and 3-25 parts of tuber of *pinellia*. The traditional Chinese medicine composition has excellent effects in lowering blood lipids and cholesterol levels, particularly in lowering blood triglyceride. The traditional Chinese medicine composition also has excellent effects in slowing formation of atherosclerotic plaques, clearing the atherosclerotic plaques, and preventing and treating atherosclerosis.

9 Claims, 7 Drawing Sheets

(56) References Cited

OTHER PUBLICATIONS

Liu, Yang et al., "Research Situation of Dachaihu Decoction in Hyperlipoidemia", Journal of Practical Traditional Chinese Internal Medicine, vol. 31, No. 6, Jun. 24, 2017 (Jun. 24, 2017), ISSN: 1671-7813, 4 pgs.
Aging Population Health Problem Writing Group, "Non-official translation: Prevention and Countermeasures of Cardiovascular and Cerebrovascular Diseases", Ultivarietas Oryzae Sativae Et Monasci, May 31, 2006, 6 pgs.
Chinese Office Action dated Jan. 5, 2022, in corresponding Application No. 202010121966.6; 18 pages (with English Translation).
Zhong Zhou et al., "Using Drug Regularity Investigation of 140 Hypolipidemic Chinese Medicines in the Treatment of Hyperlipidemia", Journal of Hunan Univ of CM, Jan. 2015, vol. 35, No. 1, 3 pgs.
Chinese Notification Grant Patent Right for Invention dated Jun. 28, 2022, in corresponding Application No. 202010121966.6; 4 pages (with English Translation).

* cited by examiner

TRADITIONAL CHINESE MEDICINE COMPOSITION, AND PREPARATION METHOD THEREFOR AND APPLICATION THEREOF

TECHNICAL FIELD

The present invention relates to the field of traditional Chinese medicines, and particularly to a traditional Chinese medicine composition, a method for preparing the same and use of the traditional Chinese medicine composition in preparing a medicament for preventing or treating increased blood lipids, increased triglyceride, increased cholesterol, hyperlipidemia and atherosclerosis.

BACKGROUND

Blood lipids is a general term for various lipid substances in blood, the most important ones of which are cholesterol and triglyceride (also referred to as neutral fat). Other important lipids include lipoproteins, which include low density lipoproteins and high density lipoproteins. The average content of blood cholesterol in healthy people is 2.8-5.17 mmol/L, and the average content of blood triglyceride is 0.56-1.7 mmol/L. Either increased cholesterol or increased triglyceride, or comorbidity of the two, can be referred to as hyperlipidemia.

The "Report on Chinese Residents' Chronic Diseases and Nutrition" released by the National Health and Family Planning Commission in early 2015 shows that the morbidity of dyslipidemia in Chinese adults in 2012 was 40.40%, greatly increased as compared to that in 2002, in which the morbidity of hypercholesterolemia was 4.9%, and the morbidity of hypertriglyceridemia was 13.1%. It represents a common exposure state to dyslipidemia in the residents, which poses a great challenge to the prevention and treatment of dyslipidemia in China.

Atherosclerosis (AS) is the leading cause of coronary heart disease, cerebral infarction and peripheral vascular disease. Hyperlipidemia is the pathological basis of atherosclerosis, and is characterized by accumulation of lipids and complex carbohydrates, hemorrhage, thrombosis, and subsequent fibrous tissue hyperplasia and calcareous deposits starting from tunica intima, and gradual disintegration and calcification in tunica media at the involved arteries, which finally leading to thickening and hardening of arterial wall and narrowing of blood vessel lumen. Such pathological changes often involve large and medium muscular arteries, and once they progress enough to obstruct the lumen of the arteries, the tissues or organs supplied by the arteries will be ischemia or necrosis. Lipids accumulating in arterial intima is yellow and atheromatous in appearance and is therefore called atherosclerosis.

Atherosclerotic cardiovascular disease is known as the "leading killer" in developed countries, and its morbidity is rapidly increasing in developing countries. Atherosclerosis contributes to a majority of deaths of coronary myocardial infarction and stroke. By 2035, more than 130 million adults (45.1%) in the U.S. are expected to suffer from certain cardiovascular diseases, the total cost of which will be up to $1.1 trillion. The morbidity and mortality of cardiovascular diseases in China are still in an increasing stage. In China, cardiovascular diseases affect about 290 million people and ranks the first in mortality, consisting of more than 30% of deaths of disease. Of course, hyperlipidemia does not necessarily mean a cardiovascular disease, but active treatment for hyperlipidemia is one of the important measures to prevent cardiovascular diseases.

Reasonable diet and proper exercise are effective and necessary measures for controlling and preventing increased blood lipids and thus reducing the harm of atherosclerotic cardiovascular diseases. However, when diet and exercise are not effective, pharmacotherapies become an inevitable choice.

At present, there are various chemical lipid-lowering agents in clinical applications, mainly including statins and fibrates. Although the specific mechanisms of these medicines are different, they mainly work by directly acting on the synthetic and metabolic pathways of fat. Due to the high recurrence rate of increased blood lipid after treatment discontinuation, the synthetic chemical lipid-lowering agents require long-term use, which causes the loss of economic resources, and greatly increases the probability of toxicities and adverse effects. For example, long-term use is often associated with adverse effects of various severities, including muscle pain, impairment of liver and kidney functions and the like. Furthermore, the use of chemical lipid-lowering agents cannot fundamentally prevent and control the development and progression of vascular plaques.

The lipid-lowering agents based on natural traditional Chinese medicines include Dantian Jiangzhi Wan (Hongxing, Guangdong), Zhibituo (DIAO, Chengdu), Xuezhikang (Weixin, Beijing) and the like. As can be seen from the instructions of these drugs, the drugs have some certain adverse effects, more or less. For example, the adverse effects of Xuezhikang include gastrointestinal discomfort such as stomachache, abdominal distension, heartburn and the like, and may sometimes include reversible increase of serum aminotransferase and creatine phosphokinase. In addition, these drugs are generally recommended in literature for combined use with chemical lipid-lowering agents, or for use in the elderly, etc.

Therefore, there is still a strong clinical need for traditional Chinese medicines in effectively preventing and treating increased blood lipids, increased triglyceride, increased cholesterol and hyperlipidemia. Meanwhile, at present, there are no therapies for preventing and controlling vascular plaques and treating atherosclerosis based on the traditional Chinese medicine. Therefore, there's a great social and market demand.

SUMMARY

The present invention is intended to provide a traditional Chinese medicine composition, a method for preparing the same and use thereof in preparing a medicament for preventing or treating increased blood lipids, increased triglyceride, increased cholesterol, hyperlipidemia, atherosclerosis and the like. Animal model studies and clinical studies showed that the traditional Chinese medicine composition disclosed herein has excellent effects in reducing blood lipids, reducing cholesterol, and particularly reducing blood triglyceride. Meanwhile, the animal model studies and the clinical studies also revealed that the traditional Chinese medicine composition disclosed herein has good effects in slowing down the formation of atherosclerotic plaques and removing the atherosclerotic plaques.

The inventor of the present invention proposed a therapy after a long-term study on the traditional Chinese medicine theory and clinical practice, which is significantly different from the theories of preventing and treating increased blood lipids, increased triglyceride, increased cholesterol, hyperlipidemia and atherosclerosis in modern medicine. It is believed that the major cause of hyperlipidemia and subsequent atherosclerosis can be summarized using the logic and language of traditional Chinese medicine as: phlegm-fluid retention in the blood. It is similar to hyperviscosity in the context of modern medicine. Hyperviscosity is not only the cause of hyperlipidemia and atherosclerosis, but also a disorder manifested by phlegm-fluid retention in the blood. Since the phlegm-fluid retention in the blood in traditional Chinese medicine refers to hyperviscosity in modern medicine, it is believed that the modulating therapies are core and effective means to prevent and treat hyperlipidemia and atherosclerosis. "Phlegm-fluid retention" is defined as water leaving meridians in *The Yellow Emperor's Classic of Internal Medicine*, i.e., a body fluid in the circulatory metabolism. Thicker body fluids are called phlegm, and the thinner ones are called fluid, which are collectively called phlegm-fluid retention. The "phlegm-fluid retention" in traditional Chinese medicine mostly refers to thick or thin liquid in the digestive tract, lung and respiratory tract, which is difficult to be metabolized, and can be continuously generated in the digestive tract or respiratory tract even if being excreted from the body. Such thick liquids may also overflow from the digestive tract and respiratory tract and stay under the skin, in the muscle, in the bone joint and even in viscera and the brain, leading to various masses, cysts and polyps. Even tumors are considered related to the phlegm-fluid retention in the body. Traditional Chinese medicine believes that many diseases are related to such thick liquids that can hardly be excreted from the body or metabolized. However, traditional Chinese medicine does not discuss that phlegm-fluid retention in the blood causes hyperviscosity.

In modern medicine, the concept of "hyperviscosity" includes dozens of biochemical indexes. For example, some indexes of hyperlipidemia (total serum cholesterol, low-density cholesterol, high-density cholesterol, translipoprotein, triglyceride), some indexes of hyperglycemia (fasting glucose, glycated hemoglobin, fasting insulin, C-peptide, glycated serum protein, fructosamine), indexes of platelets (platelet count, platelet adhesion, platelet sedimentation, etc.), some indexes of red blood cells (red blood cell count, red blood cell sedimentation, red blood cell adhesion, hematocrit, red blood cell deformability, red blood cell size), indexes of hyperviscosity (apparent viscosity, relative viscosity, reduced viscosity, specific viscosity, etc.), and some other relevant indexes (fibrinogen, immunoglobulin, etc.) may be included. These indexes are those of relatively close influence on hyperviscosity, but still not all of them. Hyperviscosity may have different manifestations. Modern medicine has not yet provided an appropriate and well-recognized pathogenic reason, and the treatments for hyperviscosity are still index-oriented therapies, for example, oral medicines for hyperlipidemia and hyperglycemia. However, because the hyperviscosity is not solved fundamentally, the hypolipidemic and hypoglycemic effects are short in duration and not curative, thus requiring long-term administration.

Phlegm-fluid retention in the blood causes hyperviscosity, which greatly increases risks of hyperlipidemia and hyperglycemia, further causes atherosclerosis, blocks blood vessels, and then causes heart, brain and kidney diseases. Based on this theory, in medical clinical practice, we developed a traditional Chinese medicine composition for effectively and durably reducing blood lipids, particularly reducing triglyceride, and for effectively preventing and treating hyperlipidemia and atherosclerosis.

The present invention provides a traditional Chinese medicine composition, comprising the following raw materials in part by weight: 10-35 parts of thorowax root, 5-25 parts of immature orange fruit, 3-20 parts of raw rhubarb, 3-20 parts of baical skullcap root, 3-20 parts of white peony root, 3-15 parts of dried ginger, 5-20 parts of leech, 3-20 parts of liquorice root, 3-20 parts of tangshen, 3-20 parts of largehead *atractylodes* rhizome and 3-25 parts of *pinellia tuber*.

Preferably, the traditional Chinese medicine composition comprises the following raw materials in part by weight: 20-30 parts of thorowax root, 10-20 parts of immature orange fruit, 5-15 parts of raw rhubarb, 5-10 parts of baical skullcap root, 5-15 parts of white peony root, 5-10 parts of dried ginger, 7-15 parts of leech, 5-15 parts of liquorice root, 5-15 parts of tangshen, 5-15 parts of largehead *atractylodes* rhizome and 10-20 parts of *pinellia tuber*.

More preferably, the traditional Chinese medicine composition disclosed herein further comprises the following raw materials in part by weight: 3-45 parts, preferably 10-35 parts of oyster shell. More preferably, on this basis, the traditional Chinese medicine composition disclosed herein further comprises the following raw materials in part by weight: 3-15 parts, preferably 5-12 parts of red yeast rice.

Preferably, the traditional Chinese medicine composition disclosed herein is prepared from the raw materials in part by weight.

More preferably, the traditional Chinese medicine composition disclosed herein is prepared from the following raw materials in part by weight: 25 parts of thorowax root, 15 parts of immature orange fruit, 10 parts of raw rhubarb, 6 parts of baical skullcap root, 10 parts of white peony root, 6 parts of dried ginger, 10 parts of leech, 10 parts of liquorice root, 10 parts of tangshen, 10 parts of largehead *atractylodes* rhizome and 15 parts of *pinellia tuber*.

More preferably, the traditional Chinese medicine composition disclosed herein is prepared from the following raw materials in part by weight: 25 parts of thorowax root, 15 parts of immature orange fruit, 10 parts of raw rhubarb, 6 parts of baical skullcap root, 10 parts of white peony root, 6 parts of dried ginger, 10 parts of leech, 10 parts of liquorice root, 10 parts of tangshen, 10 parts of largehead *atractylodes* rhizome, 15 parts of *pinellia tuber* and 30 parts of oyster shell.

More preferably, the traditional Chinese medicine composition disclosed herein is prepared from the following raw materials in part by weight: 25 parts of thorowax root, 15 parts of immature orange fruit, 10 parts of raw rhubarb, 6 parts of baical skullcap root, 10 parts of white peony root, 6 parts of dried ginger, 10 parts of leech, 10 parts of liquorice root, 10 parts of tangshen, 10 parts of largehead *atractylodes* rhizome, 15 parts of *pinellia tuber*, 30 parts of oyster shell and 10 parts of red yeast rice.

In the above composition, the part is part by weight, and the weight is calculated by crude medicines. During production, the weights can be increased or decreased proportionally. For example, the weight may be in unit kilogram or ton in large-scale production, and can be increased or decreased, but the ratio of the weights of the raw medicinal materials among the components is unchanged.

The introductions of the related raw materials of the present invention are as follows.

Thorowax root is the dried root of *Bupleurum chinense* DC. or *Bupleurum scorzonerifolium* Willd. It has the effects of harmonizing exterior and interior, soothing the liver and upraising yang.

Immature orange fruit (or immature bitter orange, immature sweet orange, fructus aurantii immaturus) is the dried young fruit of *Citrus aurantium* L. and its cultivated varieties or *Citrus×sinensis* (Fam. Rutaceae). It has the effects of resolving stagnancy of phlegm and relieving stuffiness sensation in the chest and abdomen.

Raw rhubarb is the dried root and rhizome of *Rheum palmatum* L., *Rheum tanguticum* Maxim. ex Balf. or *Rheum officinale* Baill. (Fam. Polygonaceae). It has the effects of purging heat, relaxing the bowels, reducing heat in blood, counteracting toxicity, and eliminating blood stasis and stimulating menstruation.

Baical skullcap root is the dried root of *Scutellaria baicalensis* Georgi (Fam. Labiatae). It has the effects of removing damp-heat, quenching fire, counteracting toxin, arresting bleeding, and preventing abortion.

White peony root is the dried root of *Paeonia lactiflora* Pall. (Fam. Ranunculaceae). It has the effects of pacifying the liver, relieving pain, nourishing blood and regulating menstruation, checking excessive perspiration, etc.

Dried ginger is the dried rhizome of *Zingiber officinale* (Willd.) Rosc. (Fam. Zingiberaceae). Gingers are harvested in winter with fibrous root and silt removed, and dried in the sun or at low temperature. Pieces that are cut before drying are called "dried ginger pieces". It has the effects of warming the middle, dissipating cold, promoting recovery from collapse, eliminating damp, resolving phlegm and the like.

Leech is the dried body of *Whitmania pigra* Whitman, *Hirudo mipponica* Whitman or *Whitmania acranulata* Whitman (Fam. Hirudinidae). Leeches are captured in summer and autumn, sacrificed in boiling water, and dried in the sun or at low temperature. It has the effects of breaking blood, expelling stasis, and stimulating menstruation.

Liquorice root is the dried root and rhizome of *Glycyrrhiza uralensis* Fisch. (a herbaceous perennial in Fam. Leguminosae). It is used to reinforce the function of the spleen, replenish qi, remove heat, counteract toxicity, dispel phlegm and relieve cough, alleviate spasmodic pain, and moderate drug actions in gastrointestinal tract.

Tangshen is the dried root of *Codonpsis pilosula* (Franch.) Nannf., *Codonopsis pilosula* Nannf. var. modesta (Nannf.) L. T. Shen or *Codonopsis tangshen* Oliv. (Fam. Campanulaceae). It has the effects of tonifying qi and invigorating the function of the spleen and the lung.

Largehead *atractylodes* rhizome is the dried rhizome of *Atractylodes macrocephala* Koidz. (Fam. Compositae). It has the effects of invigorating the function of the spleen, replenishing qi, eliminating dampness by diursis and arresting excessive perspiration.

Pinellia tuber is the dried tuber of *Pinellia ternata* (Thunb.) Breit. (Fam. Araceae). It has the effects of drying dampness to resolve phlegm, directing qi downward to relieve nausea and vomiting, and eliminating stuffiness in the chest and the epigastrium.

Oyster shell is the shell of *Ostrea gigas* Thunberg, *Ostrea talienwhanensis* Crosse or *Ostrea rivularis* Gould (Fam. Osteridae). It has the effects of settling tranquillizing, nourishing yin and subduing the overflowing of yang, and softening hard masses and eliminating nodulation.

Red yeast rice is obtained by mycelium of *Monascus purpureus* Went. (Fam. Aspergillaceae) parasitizing japonica rice grains. It has the effects of invigorating the function of spleen, promoting digestion, activating blood circulation and eliminating blood stasis.

The prescription of the present invention is formed by combining clinical practice on the basis of full research on the *Treatise on Cold Damage Diseases* and corresponding medicinal materials. The prescription of the present invention uses the thorowax root as the principle drug, and the thorowax root dredges the qi of the liver, such that the function of the liver can be restored to normal operation, which is the key to metabolizing fat. The thorowax root is also a very good medicine for immunity, inflammation diminishing, fever reducing and cooling. It can regulate the immune mechanism of the whole body, play a key role in restoring some key hormones to re-decompose and balance blood lipids again, and also has a good effect on the functional recovery of thyroxine. The raw rhubarb is a minister drug, which plays a key role in clearing intestinal tract and eliminating the inflammation and harmful flora in the intestinal tract. The immature orange fruit is also a minister drug, which can be used with the thorowax root to reach the upper part and lower part of viscera, and can be used with the raw rhubarb to organize the functions of intestinal tract and eliminate the inflammation and harmful flora in the intestinal tract better. The baical skullcap root is also a ministerial medicine, which is used to reduce the secretion of gastric acid and reduce gastrin, and is also used to eliminate the inflammation in the stomach and the harmful flora in the intestinal tract. The liquorice root, tangshen, white peony root, largehead *atractylodes* rhizome and *pinellia tuber* are auxiliary drugs, which are used to remove redundant mucus in intestine and stomach, reduce the source of blood viscous substances and reduce the blood viscosity. The dried ginger instead of the ginger is used in the prescription to reduce the gastrointestinal reaction of rhubarb, so that the prescription is suitable for medium-term and long-term administration, and the requirement for the treatment time for treating hyperlipidemia and arterial plaque is met. The leech contained in the prescription is used to activate blood, break stasis, eliminate the accumulation and the viscosity of various blood platelets and red blood cells in blood vessels, which is conducive to eliminating plaques in the blood vessels. The oyster shell can be added to the prescription, which is used to digest the accumulated and insufficiently digested substances in the intestine and stomach of a human. At the same time, the oyster shell can help to soften over-tired liver and better digest liver fat. The red yeast rice can be added to the prescription, which is used to increase the effect of degrading cholesterol, but it is not a key component.

The active ingredient of the traditional Chinese medicine composition disclosed herein can be obtained by extraction or other means known in the art. The active ingredient can be obtained by separately extracting the natural raw materials of the compound drug, or by jointly extracting the natural raw materials of the compound drug.

Preferably, it is prepared by a water extraction process. More preferably, the method for preparing the traditional Chinese medicine composition disclosed herein comprises: weighing raw materials, adding water with an amount 4-12 times of the raw materials, and decocting at 75-95° C. for 30-120 min to obtain a first decoction; adding water with an amount 3-10 times of the raw materials, and decocting at 75-95° C. for 30-120 min to obtain a second decoction; and combining the two decoctions, filtering and combining filtrates. More preferably, the method for preparing the traditional Chinese medicine composition disclosed herein comprises: weighing raw materials, adding water with an amount 8 times of the raw materials, and decocting at 80° C. for 60 min to obtain a first decoction; adding water with an amount 6 times of the raw materials, and decocting at 80° C. for 60 min to obtain a second decoction; and combining the two decoctions, filtering and combining filtrates. The obtained extract can be further concentrated into the form of an ointment extract, which can be a dry ointment extract or a fluid ointment extract. Preferably, it is concentrated under a reduced pressure (−0.05 Mpa, 60° C.) to a relative density of 1.05-1.15 (60° C.).

The traditional Chinese medicine composition disclosed herein can be prepared into preparations by adding pharmaceutically acceptable carriers according to requirements. The weight percentage of the extracted or processed active ingredient of the traditional Chinese medicine composition disclosed herein in the preparation is 0.1%-99.9%, and the rest is pharmaceutically acceptable carriers.

The traditional Chinese medicine composition disclosed herein can be any pharmaceutically acceptable dosage forms, including: decoction, tablet, sugar-coated tablet, film-coated tablet, enteric-coated tablet, capsule, hard capsule, soft capsule, oral liquid, lozenge, granule, electuary, pill, pulvis, ointment, pellet, suspension, powder, solution, injection, suppository, ointment, plaster, cream, spray, drop and patch. Preferably, the composition is in oral dosage form, and further preferably in the form of decoction, capsule, tablet, oral liquid, granule, pill, pulvis, pellet, ointment and the like. Most preferably, the composition is in the form of decoction, granule, capsule and tablet.

The present invention further provides use of the traditional Chinese medicine composition in preparing a medicament for preventing or treating increased blood lipids.

The present invention further provides use of the traditional Chinese medicine composition in preparing a medicament for preventing or treating increased triglyceride.

The present invention further provides use of the traditional Chinese medicine composition in preparing a medicament for preventing or treating increased cholesterol.

The present invention further provides use of the traditional Chinese medicine composition in preparing a medicament for preventing or treating hyperlipidemia.

The present invention further provides use of the traditional Chinese medicine composition in preparing a medicament for preventing or controlling vascular plaques.

The present invention further provides use of the traditional Chinese medicine composition in preparing a medicament for preventing or treating atherosclerosis.

The present invention further provides use of the traditional Chinese medicine composition in preparing a medicament for preventing or treating chronic metabolic diseases.

The present invention further provides a method for preventing or treating increased blood lipids comprising: administering to a human in need a prophylactically or therapeutically effective amount of the traditional Chinese medicine composition disclosed herein as described above.

The present invention further provides a method for preventing or treating increased triglyceride comprising administering to a human in need a prophylactically or therapeutically effective amount of the traditional Chinese medicine composition disclosed herein as described above.

The present invention further provides a method for preventing or treating increased cholesterol comprising administering to a human in need a prophylactically or therapeutically effective amount of the traditional Chinese medicine composition disclosed herein as described above.

The present invention further provides a method for preventing or treating hyperlipidemia comprising administering to a human in need a prophylactically or therapeutically effective amount of the traditional Chinese medicine composition disclosed herein as described above.

The present invention further provides a method for preventing or controlling vascular plaques comprising administering to a human in need a prophylactically or therapeutically effective amount of the traditional Chinese medicine composition disclosed herein as described above.

The present invention further provides a method for preventing or treating atherosclerosis comprising administering to a human in need a prophylactically or therapeutically effective amount of the traditional Chinese medicine composition disclosed herein as described above.

The present invention further provides a method for preventing or treating chronic metabolic diseases comprising administering to a human in need a prophylactically or therapeutically effective amount of the traditional Chinese medicine composition disclosed herein as described above.

The traditional Chinese medicine composition disclosed herein can be administered once to three times daily, and when it is prepared in a unit dose, 1-10 unit doses are administered each time. After the traditional Chinese medicine composition disclosed herein was decocted in water, the decoction can be concentrated and dried to prepare a powder for dry ointment extract. An appropriate amount of auxiliary materials were added to prepare a granule formulation (each dose contains 1250 mg of the powder for dry ointment extract equivalent to 20 g of raw materials). The granule formulation can be administered once to three times daily with 1-2 doses each time. Alternatively, the powder for dry ointment extract can be also filled into capsules or formulated into tablets (each dose contains 312.5 mg of the powder for dry ointment extract equivalent to 5 g of raw materials). The capsules or tablets can be administered once to three times daily with 2-8 capsules or tablets each time. The specific usage and dosage can be adjusted according to the specific condition of the patient.

The traditional Chinese medicine formula of the present invention is an innovative construct based on the theory and practice of "phlegm-fluid retention in the blood" and the *Treatise on Cold Damage Diseases*. The inventor of the present invention further optimized the component proportion on the basis of fully investigating and considering the properties and efficacies of the components in the formula. In particular, the formula of the present invention creatively contains dried ginger and leech with optimized proportions in clinical practice. The traditional Chinese medicine composition disclosed herein has a very significant effect on hyperviscosity, and improves the total blood viscosity through two ways. The first way is to reduce the viscous substance—phlegm-fluid retention in the intestine and stomach and reduce the cause of hyperviscosity by improving digestion of the intestine and stomach and excretion. The second way is to directly metabolize the organic components of the hyperviscosity, including blood lipids, by promoting metabolism. The traditional Chinese medicine composition disclosed herein can also reduce the aggregation degree, sedimentation degree and cutting degree of red blood cells, and reduce the aggregation degree, sedimentation degree and cutting degree of platelets. Clinical studies showed that the traditional Chinese medicine formula of the present invention has excellent efficacy in reducing blood lipids, reducing cholesterol, and particularly reducing blood triglyceride, with a response rate over 90%. It has significant effect on severe blood triglyceride elevation (triglyceride>5.6 mmol/L), which can be reduced by 90% or greater in a short time (14 days, one course of treatment). The traditional Chinese medicine formula of the present invention has excellent efficacy, which was also verified by animal model studies carried out by third-party institutions. In addition, the studies showed that the traditional Chinese medicine composition disclosed herein also has good efficacy in specifically slowing down the formation of atherosclerotic plaques and removing the atherosclerotic plaques.

BRIEF DESCRIPTION OF DRAWINGS

Embodiments of the present invention are described in detail below with reference to the accompanying drawings.

DETAILED DESCRIPTION

Figure 1:
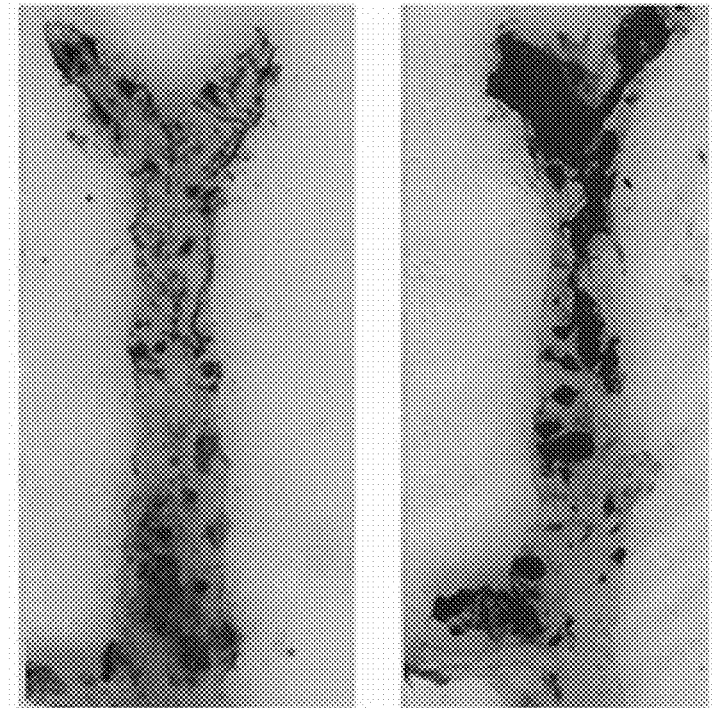
FIG. 1: comparison of Oil Red O-stained full-length aorta in ApoE$^{-/-}$ mice in the negative control group versus the atherosclerotic plaque modeling control group. A: a representative Oil Red O staining picture in the negative control group; B: a representative Oil Red O staining picture in the modeling control group after modeling.

The present invention will be further described in detail below with reference to specific embodiments, and the examples are given only for illustrating the present invention but not for limiting the scope of the present invention.

The test methods in the following examples are all conventional methods unless otherwise specified; the raw materials, reagents, materials and the like used in the following examples are all commercially available products unless otherwise specified.

In the specification of the present application, unless otherwise specified, the amount of the solvent in the preparation process of each test drug is a volume multiple based on the weight of the medicinal materials.

Example 1. Preparation of the Traditional Chinese Medicine Composition Disclosed Herein Example 1-1

The following raw materials were weighed: 25 g of thorowax root, 15 g of immature orange fruit, 10 g of raw rhubarb, 6 g of baical skullcap root, 10 g of white peony root, 6 g of dried ginger, 10 g of leech, 10 g of liquorice root, 10 g of tangshen, 10 g of largehead *atractylodes* rhizome, 15 g of *pinellia tuber* and 30 g of oyster shell. The raw materials were decocted for extraction twice in a closed container. Water with an amount 8 times of the raw materials was added for the first time, and the mixture was decocted at 80° C. for 60 min to obtain a decoction. Then water with an amount 6 times of the raw materials was added for the second time, and the mixture was decocted at 80° C. for 60 min a second decoction. The two decoctions were combined and filtered, and the filtrates were combined. The filtrate was concentrated at reduced pressure (−0.05 Mpa, 60° C.) to a relative density of 1.05-1.15 (60° C.), and lyophilized at reduced pressure to obtain a powder A for dry ointment extract with a yield of 25% relative to the raw materials.

To the obtained powder A for dry ointment extract was added β-cyclodextrin in a ratio of 4:1 to prepare powder A granules for dry ointment extract. The granules were dried, cooled and packaged as a granule formulation (each bag contained 1250 mg of the powder for dry ointment extract of the traditional Chinese medicine, equivalent to 20 g of the raw materials).

Example 1-2

The following raw materials were weighed: 25 g of thorowax root, 15 g of immature orange fruit, 10 g of raw rhubarb, 6 g of baical skullcap root, 10 g of white peony root, 6 g of dried ginger, 10 g of leech, 10 g of liquorice root, 10 g of tangshen, 10 g of largehead *atractylodes* rhizome and 15 g of *pinellia tuber*. The raw materials were decocted for extraction twice in a closed container. Water with an amount 8 times of the raw materials was added for the first time, and the mixture was decocted at 80° C. for 60 min to obtain a decoction. Then water with an amount 6 times of the raw materials was added for the second time, and the mixture was decocted at 80° C. for 60 min a second decoction. The two decoctions were combined and filtered, and the filtrates were combined. The filtrate was concentrated at reduced pressure (−0.05 Mpa, 60° C.) to a relative density of 1.05-1.15 (60° C.), and lyophilized at reduced pressure to obtain a powder B for dry ointment extract with a yield of 25% relative to the raw materials.

To the obtained powder B for dry ointment extract was added β-cyclodextrin in a ratio of 4:1 to prepare powder B granules for dry ointment extract. The granules were dried, cooled and packaged as a granule formulation (each bag contained 1250 mg of the powder for dry ointment extract of the traditional Chinese medicine, equivalent to 20 g of the raw materials).

Example 1-3

The following raw materials were weighed: 25 g of thorowax root, 15 g of immature orange fruit, 10 g of raw rhubarb, 6 g of baical skullcap root, 10 g of white peony root, 6 g of dried ginger, 10 g of leech, 10 g of liquorice root, 10 g of tangshen, 10 g of largehead *atractylodes* rhizome, 15 g of *pinellia tuber*, 10 g of red yeast rice and 30 g of oyster shell. The raw materials were decocted for extraction twice in a closed container. Water with an amount 8 times of the raw materials was added for the first time, and the mixture was decocted at 80° C. for 60 min to obtain a decoction. Then water with an amount 6 times of the raw materials was added for the second time, and the mixture was decocted at 80° C. for 60 min a second decoction. The two decoctions were combined and filtered, and the filtrates were combined. The filtrate was concentrated at reduced pressure (−0.05 Mpa, 60° C.) to a relative density of 1.05-1.15 (60° C.), and lyophilized at reduced pressure to obtain a powder C for dry ointment extract with a yield of 25% relative to the raw materials.

To the obtained powder C for dry ointment extract was added β-cyclodextrin in a ratio of 4:1 to prepare powder C granules for dry ointment extract. The granules were dried, cooled and packaged as a granule formulation (each bag contained 1250 mg of the powder for dry ointment extract of the traditional Chinese medicine, equivalent to 20 g of the raw materials).

Example 2. Study on the Effect of the Traditional Chinese Medicine Composition Disclosed Herein on Hybrid Hyperlipidemia Rat Model 2.1 Objectives: to investigate the effect of the traditional Chinese medicine composition disclosed herein on a hybrid hyperlipemia rat model.

2.2 Test compound: powder A for dry ointment extract obtained in Example 1-1. Appearance: brown powder; storage condition: 2-8° C., dryness.

2.3 Reference compound: atorvastatin calcium tablet (Lipitor). Appearance: white oval film-coated tablet; strength: 10 mg/tablet; packaging: aluminum/aluminum blister; manufacturer: Pfizer Inc.; storage condition: sealing.

2.4 Vehicle, Emulsifier and Other Media:

2.4.1 Sodium Carboxymethyl Cellulose

Storage condition: room temperature;

The method for preparing 0.5% sodium carboxymethyl cellulose solution: 5.0 g of CMC-Na was accurately weighed and slowly added to a beaker containing about 800 mL of purified water, and the mixture was stirred by a magnetic stirrer at room temperature until the CMC-Na was dissolved. The solution was let stand at 2-8° C. overnight, and diluted to 1000 mL. The resulting solution was mixed well, and stored at 2-8° C. for later use.

2.4.2 Name: Purified Water

Manufacturer: Laboratory of Comparative Medicine, Guangdong Medical Laboratory Animal Center.

2.5 Main Instruments and Reagents

BS-3000A electronic analytical balance, sensitivity: 0.1 g, Shanghai Yousheng Weighing Apparatus Co., Ltd.;

BS224S electronic analytical balance, sensitivity: 0.1 mg, Sartorius Scientific Instruments (Beijing) Co., Ltd.;

5418 benchtop high-speed centrifuge, EPPENDORF, Germany;

7020 automatic biochemical analyzer, Hitachi High-tech Corporation;

Isoflurane: batch No. 217171101, expiration date: Nov. 1, 2020, Shenzhen RWD Life Science Co., Ltd.;

Urethane: batch No. 20160920, expiration date: Sep. 20, 2021, Sinopharm Chemical Reagent Co., Ltd.;

Sodium chloride injection: batch No. H18052802-2, Guangdong Kelun Pharmaceutical Co., Ltd.;

20% urethane solution for anesthesia: 20.0 g of urethane was added to 100 mL of sodium chloride injection, and the mixture was mixed well and sterilized through a 0.2 μm filter membrane;

TC kit: batch Nos. 20180722 and 20190222, expiration date: Jan. 10, 2020 and Aug. 20, 2020, Shanghai Kehua Bio-Engineering Co., Ltd.;

TG kit: batch Nos. 20180822 and 20190222, expiration date: Feb. 23, 2020 and Aug. 25, 2020, Shanghai Kehua Bio-Engineering Co., Ltd.;

HDL-C kit: batch No. 20181012, expiration date: Oct. 11, 2019, Shanghai Kehua Bio-Engineering Co., Ltd.;

LDL-C kit: batch No. 20190212, expiration date: Feb. 26, 2020, Shanghai Kehua Bio-Engineering Co., Ltd.

2.6 Experimental System

Species: SD rat; grade: SPF grade; male, 190.2-223.9 g;

Source and certifications: purchased from the Guangdong Medical Laboratory Animal Center, Animal Production License No. SCXK (Guangdong) 2018-0002, Animal Certificate No. 44007200066274;

Identification: The animal was numbered with saturated picric acid through hair dyeing, and the hair on different parts of the body surface of animal was painted with dyeing spots to indicate different numbers. Animals were identified through skin staining and cage labels.

Animal welfare: The tests and procedures related to the animal experiment involved in this study followed the relevant laws and regulations for use and management of the experimental animals and the relevant regulations of the institutional animal ethical committee to ensure the welfare of the experimental animals.

Euthanasia: The eliminated animals after modeling were sacrificed by carbon dioxide inhalation. After the study, the animals were anesthetized by intraperitoneal injection of 20% urethane solution at 6 mL/kg body weight and then euthanized by exsanguination. The corpses were temporarily stored in a corpse freezer before disposal.

Quarantine: The purchased rats were quarantined for 3 days and observed for once daily, and no unhealthy animals were found.

Housing and management: the animals were housed in the SPF grade animal room of Guangdong Medical Laboratory Animal Center. Laboratory Animal Use License No. SYXK (Guangdong) 2018-0002; Animal Experiment Certificate No. 00219646. Animal housing conditions: group housing, 5 animals/cage; temperature and humidity: 20-26° C., 40%-70%; 12 h/12 h light/dark cycle; the condition of the housing room was always kept stable to ensure the reliability of the experimental results. During the experiment, the animals were fed with the corresponding granulated feed according to the experimental requirements, and were given free access to food and water.

2.7 Dosage and Grouping

Dosage: In a pre-test, 4 SD rats were intragastrically administered with the test compound at doses of 2000 mg/kg body weight and 5000 mg/kg body weight. No animal died within 72 h. The dose of the test compound in adult human is 5 g/day. As per 60 kg body weight of an adult, 5 times and 10 times of the recommended dose for human were used as the test doses, and the test doses were 417 mg/kg body weight and 833 mg/kg body weight, respectively. The clinical dose of the reference drug atorvastatin calcium tablet is 10 mg/day. As per 60 kg body weight of an adult. 20 times of the recommended dose for human body was used as the test dose of the reference drug, that is, the test dose of the reference drug atorvastatin calcium tablet was 3.3 mg/kg body weight.

Grouping: After quarantine, the animals were randomized into a negative control group of 10 animals and modeling groups of the rest. After the modeling groups were given modeling feed for 2 weeks, the animals were anesthetized by isoflurane inhalation without fasting. The blood was collected from orbital venous sinus and was centrifuged at 3000 rpm for 10 min to separate the serum. The total cholesterol (TC), triglyceride (TG), low-density lipoprotein cholesterol (LDL-C) and high-density lipoprotein cholesterol (HDL-C) levels were determined. Animals with lower TG levels were eliminated. 40 animals were selected and randomized into the modeling control group, the positive control group, and test compound 417 mg/kg and 833 mg/kg groups according to the TG levels, with 10 animals in each group.

2.8.4 Modeling: The negative control group was given the maintenance feed and the remaining groups were given the modeling feed until the end of the study. Except for the negative control group, the other groups were given a western high-fat feed from d30 to d36 of during the treatment period.

2.8.5 Administration: After the modeling was finished, the positive control group and the test compound 417 mg/kg and 833 mg/kg groups with test samples were intragastrically administered with corresponding dose of medical liquid by 10 mL/kg body weight every day, and the negative control group and the modeling control group were administered with purified water of the same volume for 67-68 days (the first 5 animals in each group were administered for 67 days, and the last 5 animals in each group were administered for 68 days).

2.8.6 Measurements 2.8.6.1 General state: The clinical states of the animals were observed once daily until the end of study.

2.8.6.2 Body weight: The body weight of the animals was measured once at the start and end of study and once weekly during the study.

2.8.6.3 Blood lipids: After 2, 4, 7 and 9 weeks of treatment (d14, d28, d52 and d65), the animals were anesthetized by

TABLE 1

Dosage and grouping

| Group | n | Dose (mg/kg body weight) | Equivalent recommended dose for human | Route of administration and volume | Concentration of solution (mg/mL) |
|---|---|---|---|---|---|
| Negative control group | 10 | — | — | Intragastric, once daily 10 mL/kg body weight | — |
| Modeling control group | 10 | — | — | Intragastric, once daily 10 mL/kg body weight | — |
| Positive control group | 10 | 3.3 | 20 times | Intragastric, once daily 10 mL/kg body weight | 0.33 |
| Test compound 417 mg/kg group | 10 | 417 | 5 times | Intragastric, once daily 10 mL/kg body weight | 41.7 |
| Test compound 833 mg/kg group | 10 | 833 | 10 times | Intragastric, once daily 10 mL/kg body weight | 83.3 |

2.8 Methodology 2.8.1 High-fat and high-cholesterol modeling feed: A maintenance feed containing 20.0% of sucrose, 5% of lard, 1.0% of cholesterol, 0.1% of sodium cholate, appropriate amounts of casein, calcium bicarbonate, powdered stone and the like. Other than crude fat, in the modeling feed, moisture, crude protein, crude fat, crude fiber, crude ash, calcium, phosphorus and calcium:phosphorus all satisfied the national standard for maintenance feed. The feed was provided by Guangdong Medical Laboratory Animal Center.

2.8.2 Preparation of the test compound solution: a proper amount of the test compound was added into a volumetric flask, and ground and dissolved in a small amount of purified water. The mixture was brought to the volume with purified water and stirred for complete dissolution to obtain a concentration of 166.7 mg/mL. The solution was sequentially diluted to concentrations of 83.3 mg/mL and 41.7 mg/mL.

2.8.3 Preparation of the reference drug solution: 1 atorvastatin calcium tablet (strength: 10 mg/tablet) was added into a volumetric flask, and ground and dissolved in a 0.5% CMC-Na solution. The mixture was brought to 60 mL with the 0.5% CMC-Na solution to obtain a concentration of about 0.33 mg/mL. The solution was shaken to mix well before use.

isoflurane inhalation without fasting. The blood was collected from orbital venous sinus and centrifuged at 3000 rpm for 10 min to separate the serum. The TC, TG, LDL-C and HDL-C levels were determined.

2.8.6.4 The first 5 animals in each group were fasted overnight on d66, and the last 5 animals on d67. The animals were treated, weighed and anesthetized by intraperitoneal injection of a 20% urethane solution at 6 mL/kg body weight on the next day. The blood was collected from abdominal aorta, and the serum was separated and cryopreserved. The animals were sacrificed by exsanguination. The testis and perirenal fat tissues were weighed. A part of the liver was fixed in neutral formaldehyde, and the rest of the liver was cryopreserved in liquid nitrogen.

2.9 Statistics: The data are represented by ($\bar{x}$±s). The statistical analysis was carried out using SPSS 21.0 software; The pairwise comparison was conducted by one-way analysis of variance with a test level $\alpha$=0.05.

2.10 Results 2.10.1 General observation: During the study, no abnormal reaction was observed in the body shape, hair, skin, feces, muscle tension, gait, spirit, respiration and the like of the animals.

2.10.2 Body weight (see Table 2): During the study, there was no statistical difference ($P>0.05$) in the body weight of the animals in each group.

2.10.3 Blood Lipids (See Tables 3-7)

2.10.3.1 Blood lipids at baseline after modeling (see Table 3): compared with the negative control group, the increases in serum TC, TG and LDL-C values in the modeling control group at baseline after modeling were significantly different (P<0.05 or 0.01); compared with the modeling control group, the four measurements for blood lipids in each group at baseline after modeling had no significant difference (P>0.05).

2.10.3.2 Blood lipids at week 2 of treatment (see Table 4): compared with the negative control group, the increases in serum TC, TG and LDL-C values in the modeling control group at week 2 of treatment were significantly different (P<0.05 or 0.01); compared with the modeling control group, the decreases in serum TC, TG, HDL-C and LDL-C values in the positive control group at week 2 of treatment had no significant difference (P>0.05); compared with the modeling control group, the serum measurements in the test compound 417 mg/kg and 833 mg/kg groups at week 2 of treatment had no significant difference (P>0.05). Compared with the modeling control group, the TG mean was reduced from 3.22 mmol/L in the modeling control group to 2.89 mmol/L in the test compound 417 mg/kg group and 2.51 mmol/L in the test compound 833 mg/kg group, but the reduction was not statistically significant (the P value was between 0.05 and 0.1).

2.10.3.3 Blood lipids at week 4 of treatment (see Table 5): compared with the negative control group, the increases in serum TC, TG and LDL-C values in the modeling control group at week 4 of treatment were significantly different (P<0.05 or 0.01); compared with the modeling control group, the decreases in serum TC and LDL-C values in the positive control group at week 4 of treatment had changes close to statistical difference (P=0.10 for TC and P=0.05 for LDL-C); compared with the modeling control group, the decreases in TG and LDL-C values in the test compound 833 mg/kg group at week 4 of treatment had statistically significant difference (P<0.05). In the test compound 417 mg/kg group, TG and LDL-C values showed decrease trend at week 4 of treatment, which were not statistically significant (P>0.05). TG decreased from 3.03 mmol/L in the modeling control group to 2.32 mmol/L (P=0.05). At the same time, the test compound also demonstrated a decreasing trend in TC. TC decreased from 3.44 mmol/L in the modeling control group to 2.72 mmol/L (the test compound 417 mg/kg group, P=0.08) and 2.75 mmol/L (the test compound 833 mg/kg group, P=0.09).

2.10.3.4 Blood lipids at week 7 of treatment (see Table 6): compared with the negative control group, the increases in serum TC and LDL-C values in the modeling control group at week 7 of treatment were significantly different (P<0.01), and TG value had an increasing trend which was not statistically significant (P>0.05); the serum TC value in the positive control group at week 7 of treatment was 3.03 mmol/L, and compared with the modeling control group (3.55 mmol/L), the decrease was not statistically significant (P=0.10); compared with the modeling control group, the decreases of serum TG in the test compound 417 mg/kg and 833 mg/kg groups at week 7 of treatment had significant or nearly significant statistical differences (the P values of test compound 417 mg/kg and 833 mg/kg groups were P=0.05 and P=0.04, respectively). Also, there was no statistically significant difference (P<0.05) in the decrease of LDL-C in the test compound 833 mg/kg group.

2.10.3.5 Blood lipids at week 9 of treatment (see Table 7): compared with the negative control group, the increases in serum TC, TG and LDL-C values in the modeling control group at week 9 of treatment were significantly different (P<0.01); compared with the modeling control group, the decreases in serum TC, TG and LDL-C values in the positive control group at week 9 of treatment had no significant difference (P>0.05); compared with the modeling control group, the four serum lipid measurements in the test compound 417 mg/kg group at week 9 of treatment had no significant difference (P>0.05). However, the decreases in TC, TG and LDL-C in the test compound 833 mg/kg group had statistically significant difference (P<0.05) at week 9 of treatment.

2.10.4 Weight and coefficient of organ/tissue (see Table 8): compared with the negative control group, the increases of the weight and coefficient of liver in rats in the modeling control group were statistically significant (P<0.01); compared with the modeling control group, the weight and the coefficient of liver in the positive control group had no statistically significant difference (P<0.05 or 0.01); compared with the modeling control group, the weights and coefficients of organs/tissues in the test compound 417 mg/kg and 833 mg/kg groups had no statistically significant difference (P>0.05). The organs were preserved.

TABLE 2

Effect of the traditional Chinese medicine composition disclosed herein on body weight of rats with hybrid hyperlipidemia ($\bar{x} \pm s$, g, n = 10)

| Group | Before modeling | D1 of treatment | D7 of treatment | D14 of treatment | D21 of treatment | D28 of treatment |
|---|---|---|---|---|---|---|
| Negative control group | 210.8 ± 7.1 | 345.8 ± 18.4 | 386.7 ± 22.6 | 423.1 ± 26.2 | 456.7 ± 32.4 | 471.3 ± 31.0 |
| Modeling control group | 208.7 ± 9.4 | 330.1 ± 12.5 | 364.1 ± 13.1 | 404.8 ± 17.8 | 435.1 ± 19.7 | 468.9 ± 23.6 |
| Positive control group | 212.3 ± 8.3 | 331.5 ± 21.2 | 363.9 ± 21.2 | 401.4 ± 17.7 | 424.8 ± 24.5 | 454.2 ± 30.7 |
| Test compound 417 mg/kg group | 208.2 ± 6.6 | 335.0 ± 24.7 | 366.9 ± 26.2 | 405.9 ± 31.7 | 429.1 ± 31.7 | 463.3 ± 37.1 |
| Test compound 833 mg/kg group | 210.1 ± 4.9 | 342.7 ± 16.3 | 375.0 ± 18.8 | 410.5 ± 18.9 | 443.0 ± 22.2 | 475.7 ± 26.6 |

| Group | D35 of treatment | D42 of treatment | D51 of treatment | D56 of treatment | D63 of treatment |
|---|---|---|---|---|---|
| Negative control group | 487.3 ± 29.8 | 512.2 ± 29.1 | 548.2 ± 34.4 | 556.4 ± 35.8 | 578.7 ± 36.8 |
| Modeling control group | 500.2 ± 26.6 | 531.4 ± 29.5 | 563.4 ± 30.4 | 578.3 ± 32.3 | 586.5 ± 31.8 |
| Positive control group | 485.8 ± 33.6 | 523.4 ± 42.1 | 557.4 ± 48.0 | 566.7 ± 52.5 | 577.3 ± 55.9 |

TABLE 2-continued

Effect of the traditional Chinese medicine composition disclosed herein on body weight of rats with hybrid hyperlipidemia ($\bar{x} \pm s$, g, n = 10)

| | | | | | |
|---|---|---|---|---|---|
| Test compound 417 mg/kg group | 489.8 ± 40.8 | 518.0 ± 56.0 | 554.1 ± 53.6 | 559.4 ± 52.3 | 578.7 ± 56.5 |
| Test compound 833 mg/kg group | 509.0 ± 28.9 | 546.3 ± 34.5 | 583.9 ± 34.7 | 592.5 ± 37.8 | 610.5 ± 40.7 |

Note: statistical analysis was based on repeated measurements.

TABLE 3

Effect of the traditional Chinese medicine composition disclosed herein on blood lipid of rats with hybrid hyperlipidemia (at baseline after modeling; $\bar{x} \pm s$, mmol/L, n = 10)

| Group | TC | TG | HDL-C | LDL-C |
|---|---|---|---|---|
| Negative control group | 1.96 ± 0.19 | 2.43 ± 0.54 | 0.71 ± 0.08 | 0.35 ± 0.03 |
| Modeling control group | 4.19 ± 0.47▲▲ | 3.08 ± 0.74▲ | 0.69 ± 0.07 | 1.17 ± 0.31▲▲ |
| Positive control group | 4.11 ± 0.51 | 3.09 ± 0.75 | 0.77 ± 0.12 | 1.04 ± 0.33 |
| Test compound 417 mg/kg group | 4.01 ± 0.58 | 3.17 ± 0.84 | 0.68 ± 0.22 | 1.03 ± 0.27 |
| Test compound 833 mg/kg group | 4.25 ± 0.64 | 3.11 ± 0.85 | 0.78 ± 0.11 | 1.07 ± 0.17 |

Note: compared between groups, independent sample T test; "▲"indicates P < 0.05, "▲▲"indicates P < 0.01, and "#"indicates P between 0.05 and 0.10

TABLE 4

Effect of the traditional Chinese medicine composition disclosed herein on blood lipid of rats with hybrid hyperlipidemia (at week 2 of treatment; $\bar{x} \pm s$, mmol/L, n = 10)

| Group | TC | TG | HDL-C | LDL-C |
|---|---|---|---|---|
| Negative control group | 1.79 ± 0.22 | 2.51 ± 0.32 | 0.61 ± 0.07 | 0.38 ± 0.05 |
| Modeling control group | 3.79 ± 0.68▲▲ | 3.22 ± 0.93▲ | 0.60 ± 0.09 | 1.51 ± 0.46▲▲ |
| Positive control group | 3.84 ± 0.57 | 3.02 ± 0.91 | 0.63 ± 0.07 | 1.33 ± 0.47 |
| Test compound 417 mg/kg group | 3.80 ± 0.61 | 2.89 ± 0.76 | 0.60 ± 0.08 | 1.37 ± 0.28 |
| Test compound 833 mg/kg group | 4.07 ± 0.44 | 2.51 ± 0.68# | 0.68 ± 0.09# | 1.37 ± 0.22 |

Note: compared between groups, independent sample T test; "▲"indicates P < 0.05, "▲▲"indicates P < 0.01, and "#"indicates P between 0.05 and 0.10

TABLE 5

Effect of the traditional Chinese medicine composition disclosed herein on blood lipid of rats with hybrid hyperlipidemia (at week 4 of treatment; $\bar{x} \pm s$, mmol/L, n = 10)

| Group | TC | TG | HDL-C | LDL-C |
|---|---|---|---|---|
| Negative control group | 1.42 ± 0.18 | 2.27 ± 0.66 | 0.53 ± 0.05 | 0.19 ± 0.03 |
| Modeling control group | 3.44 ± 0.99▲▲ | 3.03 ± 0.83▲ | 0.53 ± 0.13 | 1.18 ± 0.46▲▲ |
| Positive control group | 2.75 ± 0.77# | 3.02 ± 1.23 | 0.50 ± 0.10 | 0.79 ± 0.36# |
| Test compound 417 mg/kg group | 2.72 ± 0.71# | 2.32 ± 0.70# | 0.44 ± 0.07# | 0.89 ± 0.28# |
| Test compound 833 mg/kg group | 2.75 ± 0.72# | 2.33 ± 0.63▲ | 0.45 ± 0.13 | 0.85 ± 0.15▲ |

Note: compared between groups, independent sample T test; "▲"indicates P < 0.05, "▲▲"indicates P < 0.01, and "#"indicates P between 0.05 and 0.10

TABLE 6

Effect of the traditional Chinese medicine composition disclosed herein on blood lipid of rats with hybrid hyperlipidemia (at week 7 of treatment; $\bar{x} \pm s$, mmol/L, n = 10)

| Group | TC | TG | HDL-C | LDL-C |
|---|---|---|---|---|
| Negative control group | 2.08 ± 0.33 | 2.66 ± 0.51 | 0.71 ± 0.07 | 0.26 ± 0.02 |

TABLE 6-continued

Effect of the traditional Chinese medicine composition disclosed herein on blood lipid of rats with hybrid hyperlipidemia (at week 7 of treatment; $\bar{x} \pm s$, mmol/L, n = 10)

| Group | TC | TG | HDL-C | LDL-C |
|---|---|---|---|---|
| Modeling control group | 3.55 ± 0.66▲▲ | 3.39 ± 1.12 | 0.69 ± 0.11 | 0.79 ± 0.27▲▲ |
| Positive control group | 3.03 ± 0.68 | 3.30 ± 1.40 | 0.65 ± 0.07 | 0.65 ± 0.25 |
| Test compound 417 mg/kg group | 3.23 ± 0.72 | 2.39 ± 1.01# | 0.66 ± 0.07 | 0.64 ± 0.20 |
| Test compound 833 mg/kg group | 3.17 ± 0.51 | 2.49 ± 0.66▲ | 0.67 ± 0.11 | 0.56 ± 0.08▲ |

Note:
compared between groups, independent sample T test; "▲"indicates P < 0.05, "▲▲"indicates P < 0.01, and "#"indicates P between 0.05 and 0.10

TABLE 7

Effect of the traditional Chinese medicine composition disclosed herein on blood lipid of rats with hybrid hyperlipidemia (at week 9 of treatment; $\bar{x} \pm s$, mmol/L, n = 10)

| Group | TC | TG | HDL-C | LDL-C |
|---|---|---|---|---|
| Negative control group | 1.93 ± 0.27 | 2.69 ± 0.53 | 0.63 ± 0.04 | 0.35 ± 0.09 |
| Modeling control group | 3.66 ± 0.55▲▲ | 3.62 ± 0.83▲ | 0.65 ± 0.11 | 1.19 ± 0.40▲▲ |
| Positive control group | 3.58 ± 0.88 | 3.78 ± 1.76 | 0.69 ± 0.10 | 1.23 ± 0.48 |
| Test compound 417 mg/kg group | 3.29 ± 0.87 | 3.34 ± 1.47 | 0.65 ± 0.08 | 1.11 ± 0.47 |
| Test compound 833 mg/kg group | 3.19 ± 0.41▲ | 2.59 ± 0.67▲▲ | 0.68 ± 0.12 | 0.82 ± 0.14▲ |

Note:
compared between groups, independent sample T test; "▲"indicates P < 0.05, and "▲▲"indicates P < 0.01

TABLE 8

Effect of the traditional Chinese medicine composition disclosed herein on weight and coefficient of organ/tissue in rats with hybrid hyperlipidemia ($\bar{x} \pm s$, n = 10)

| Group | Day of dissection Body weight (g) | Liver weight (g) | Perirenal fat Weight (g) | Weight of fat in testicle and around epididymis (g) | Liver coefficient | Perirenal fat Coefficient | Coefficient of fat in testicle and around epididymis |
|---|---|---|---|---|---|---|---|
| Negative control group | 563.7 ± 36.8 | 14.21 ± 1.55 | 12.59 ± 2.79 | 10.75 ± 2.80 | 2.52 ± 0.18 | 2.22 ± 0.43 | 1.90 ± 0.45 |
| Modeling control group | 577.5 ± 28.3 | 22.16 ± 3.43▲▲ | 15.13 ± 5.03 | 12.62 ± 3.20 | 3.84 ± 0.57▲▲ | 2.61 ± 0.85 | 2.18 ± 0.53 |
| Positive control group | 570.9 ± 56.2 | 20.15 ± 3.80 | 14.81 ± 4.58 | 12.07 ± 5.00 | 3.51 ± 0.42 | 2.65 ± 1.01 | 2.06 ± 0.68 |
| Test compound 417 mg/kg group | 568.5 ± 57.7 | 20.66 ± 4.16 | 13.88 ± 5.11 | 10.41 ± 3.86 | 3.62 ± 0.50 | 2.40 ± 0.69 | 1.81 ± 0.53 |
| Test compound 833 mg/kg group | 604.0 ± 40.5 | 22.07 ± 2.68 | 17.48 ± 2.33 | 13.42 ± 1.92 | 3.65 ± 0.38 | 2.90 ± 0.37 | 2.22 ± 0.31 |

Note:
compared between groups, independent sample T test; "▲"indicates P < 0.05, and "▲▲"indicates P < 0.01

2.11 Summary:

1) There was no statistical difference (P>0.05) in the body weight of the animals in each group.

2) Comparing with the negative control group, the serum TC, TG and LDL-C values in the modeling control group at baseline after modeling and at weeks 2, 4 and 9 of treatment were increased (P<0.05 or 0.01). The hybrid hyperlipemia rat model was established.

3) Compared with the modeling control group, at each time point, the positive control group demonstrated certain effects on reducing the serum total cholesterol in the rats, which, however, were not significant, indicating that the reference drug atorvastatin has no significant effect on reducing the blood lipids in the hybrid hyperlipidemia rat model and is not an ideal therapy.

4) The traditional Chinese medicine composition disclosed herein started to demonstrate an effect of reducing TG at week 2 of treatment, especially in the 833 mg/kg group, and the effects of reducing TG at weeks 4, 7 and 9 of treatment was statistically significant (P<0.05). Meanwhile, the 833 mg/kg group also showed a preliminary effect of reducing TC, and particularly, the effect of reducing TC was statistically different (P<0.05) at week 9 of treatment. The effect on reducing TG in the 417 mg/kg group at weeks 4, 7 and 9 of treatment was at the critical point for statistical difference in the statistical tests (P value between 0.05 and 0.10).

5) Compared with the negative control group, the weight and coefficient of the liver in the modeling control group were increased (P<0.01); compared with the modeling control group, the weight and coefficient of the organ/tissue in the test compound groups had no statistically significant different (P>0.05). The organs were preserved for future delivery to the sponsor.

6) Conclusion: under the experimental conditions, the animal studies showed that the traditional Chinese medicine composition disclosed herein has significant effects on reducing blood lipids and reducing cholesterol, and particularly has a significant effect on reducing blood triglyceride. Meanwhile, the effect on reducing blood lipids has certain association with the dose.

Example 3. Study of the Effect of the Traditional Chinese Medicine Composition Disclosed Herein on Formation of Atherosclerotic Plaques of ApoE$^{-/-}$ Mice 3.1 Objectives: to investigate the effect of the traditional Chinese medicine composition disclosed herein on the formation of atherosclerotic plaques in an ApoE$^{-/-}$ mouse atherosclerotic plaque model.

3.2 Test compound: powder A for dry ointment extract obtained in Example 1-1. Appearance: brown powder; storage condition: 2-8° C., dryness.

3.3 Reference drug: Rosuvastatin calcium tablet (Crestor); appearance: pink film-coated tablet; strength/purity: 10 mg/tablet; packaging: aluminum-plastic blister; manufacturer: AstraZeneca Pharmaceuticals (China) Co., Ltd.; storage conditions: sealing and dryness.

3.4 Vehicle, Emulsifier and Other Media:

3.4.1 Sodium Carboxymethyl Cellulose

Storage condition: room temperature;

The method for preparing 0.5% sodium carboxymethyl cellulose solution: 5.0 g of CMC-Na was accurately weighed and slowly added to a beaker containing about 800 mL of purified water, and the mixture was stirred by a magnetic stirrer at room temperature until the CMC-Na was dissolved. The solution was let stand at 2-8° C. overnight, and diluted to 1000 mL. The resulting solution was mixed well, and stored at 2-8° C. for later use.

3.4.2 Name: Purified Water

Manufacturer: Laboratory of Comparative Medicine, Guangdong Medical Laboratory Animal Center.

3.5 Main Instruments and Reagents

BS-3000A electronic analytical balance, sensitivity: 0.1 g, Shanghai Yousheng Weighing Apparatus Co., Ltd.;

BS224S electronic analytical balance, sensitivity: 0.1 mg, Sartorius Scientific Instruments (Beijing) Co., Ltd.;

5418 benchtop high-speed centrifuge, EPPENDORF, Germany;

7020 automatic biochemical analyzer, Hitachi High-tech Corporation;

Isoflurane: batch No. 217171101, expiration date: Nov. 1, 2020, Shenzhen RWD Life Science Co., Ltd.;

Urethane: batch No. 20160920, expiration date: Sep. 20, 2021, Sinopharm Chemical Reagent Co., Ltd.;

Sodium chloride injection: batch No. H18052802-2, Guangdong Kelun Pharmaceutical Co., Ltd.;

20% urethane solution for anesthesia: 20.0 g of urethane was added to 100 mL of sodium chloride injection, and the mixture was mixed well and sterilized through a 0.2 μm filter membrane;

TC, TG, HDL-C, LDL-C kits: Shanghai Kehua Bio-Engineering Co., Ltd.;

Quality control serum: Randox Laboratories Limited 3.6 Experimental System

Species and grade: SPF grade, ApoE$^{-/-}$ mouse; 6 ApoE mice, female, aged 28-35 days; 48 ApoE mice, half male and half female, aged 49-56 days.

Identification: The mice were identified by ear tags. Before perforation, the ear of animal and the perforation device were disinfected. Then, the ear of the animal was perforated, and an ear tag with the number of the animal was attached.

Animal welfare: The tests and procedures related to the animal experiment involved in this study followed the relevant laws and regulations for use and management of the experimental animals and the relevant regulations of the institutional animal ethical committee to ensure the welfare of the experimental animals.

Euthanasia: after end of the study, the animals were anesthetized by isoflurane inhalation. Blood was collected from eyeball, the mice were sacrificed by cervical dislocation, and specimens were collected. The corpses were temporarily stored in a corpse freezer before disposal.

Quarantine: The purchased mice were quarantined for 7 days. During the period, the animals were tested once daily. If unhealthy animals were found, the animals were immediately removed, and healthy animals would be supplemented.

Housing and management: the animals were housed in the SPF grade animal room of Guangdong Medical Laboratory Animal Center. Laboratory Animal Use License No. SYXK (Guangdong) 2018-0002. Animal housing conditions: 1 animals/cage; temperature and humidity: 20-26° C., 40%-70%; 12 h/12 h light/dark cycle; the condition of the housing room was always kept stable to ensure the reliability of the experimental results. During the study, the animals were fed with the corresponding granulated feed according to the experimental requirements, and the feeds were provided by Guangdong Medical Laboratory Animal Center. Animals were given free access to food and water.

3.7 Dosage and Grouping

Dosage: In a pre-test, 4 SD rats (half female and half male) were intragastrically administered with the test compound at doses of 2000 mg/kg body weight and 5000 mg/kg body weight. No animal died within 72 h. According to the information provided by the sponsor, the dose of the test compound in adult human is 5 g/day. As per 60 kg body weight of an adult, 10 times and 20 times of the recommended dose for human were used as the test doses, and the doses were 833 mg/kg body weight and 1667 mg/kg body weight for the test compound groups 1 and 2, respectively. The maximum clinical daily dose of the reference drug rosuvastatin calcium tablet is 20 mg. As per 60 kg body weight of an adult. 20 times of the recommended dose for human body was used as the test dose of the reference drug, that is, the test dose of the reference drug rosuvastatin calcium tablet was 6.6 mg/kg body weight.

Grouping: After quarantine, the mice were housed for 1 week in a conventional way. For the first grouping (modeling period), 6 ApoE$^{-/-}$ mice were randomized into the negative control group and were given the maintenance feed. The other 48 ApoE$^{-/-}$ mice were randomized into the modeling groups and were given 21% high-fat feed for 1 month. The blood was collected to determine the four blood lipid measurements. For the second grouping (treatment period), ApoE$^{-/-}$ mice were randomized into the modeling control group, the positive control group, the test compound 833 mg/kg group, the test compound 1667 mg/kg group according to the TC levels, with 12 mice in each group, half male and half female.

TABLE 9

Dosage and grouping

| Group | n | Dose (mg/kg body weight) | Gender | Equivalent recommended dose for human | Route of administration and volume | Concentration of solution (mg/mL) |
|---|---|---|---|---|---|---|
| Negative control group | 6 | — | ♂ | — | Intragastric, once daily, 20 mL/kg body weight | — |
| Modeling control group | 12 | — | ♂/♀ | — | Intragastric, once daily, 20 mL/kg body weight | — |
| Positive control group | 12 | 3.3 | ♂/♀ | 20 times | Intragastric, once daily, 20 mL/kg body weight | 0.33 |
| Test compound 833 mg/kg group | 12 | 833 | ♂/♀ | 10 times | Intragastric, once daily, 20 mL/kg body weight | 41.65 |
| Test compound 1667 mg/kg group | 12 | 1667 | ♂/♀ | 20 times | Intragastric, once daily, 20 mL/kg body weight | 83.35 |

3.8 Methodology 3.8.1 High-fat and high-cholesterol modeling feed: A maintenance feed containing 20.0% of sucrose, 5% of lard, 1.0% of cholesterol, 0.1% of sodium cholate, appropriate amounts of casein, calcium bicarbonate, powdered stone and the like. Other than crude fat, in the modeling feed, moisture, crude protein, crude fat, crude fiber, crude ash, calcium, phosphorus and calcium:phosphorus all satisfied the national standard for maintenance feed. The feed was provided by Guangdong Medical Laboratory Animal Center.

3.8.2 Preparation of the test compound solution: A proper amount of the test compound was ground and dissolved in a small amount of purified water. The mixture was transferred to a volumetric flask, brought to the volume with purified water and stirred for complete dissolution to obtain an 83.35 mg/mL solution for the test compound group 2. The solution was 2-fold diluted to about 41.65 mg mL for the test compound group 1.

3.8.3 Preparation of the reference drug solution: 1 rosuvastatin calcium tablet (strength: 10 mg/tablet) was ground and dissolved in a 0.5% CMC-Na solution. The mixture was transferred into a volumetric flask and brought to 30 mL with the 0.5% CMC-Na solution to obtain a concentration of about 0.33 mg/mL. The solution was shaken to mix well before use.

3.8.4 Modeling: The negative control group was given the maintenance feed and the remaining groups were given the 21% high-fat feed until the end of the study.

3.8.5 Administration: Mice in the positive control group, the test compound 833 mg/kg group and the test compound 1667 mg/kg group were intragastrically administered with the corresponding drug solution at 20 mL/kg body weight daily, and mice in the negative control group and the modeling control group were administered with purified water of the same volume once daily for 60 days.

3.8.6 Measurements:

1) General state: The general clinical states of the mice were observed and recorded once daily.

2) Body weight: The body weight was measured once at the start and end of the study and once weekly during the study. The weight gain on D30 of treatment (D29 of treatment—D1 of treatment) and D60 of treatment (D60 of treatment—D1 of treatment) was calculated.

3) TC, TG, LDL-C and HDL-C levels: After the modeling period was finished, the animals were anesthetized by isoflurane inhalation without fasting. The blood was collected from orbital venous plexus, and centrifuged at 3000 r/min at a low temperature for 10 min. The serum was separated to determine the total cholesterol TC, triglyceride TG, high-density lipoprotein HDL-C and low-density lipoprotein LDL-C levels, and the remaining serum samples were stored in a freezer at −80° C.

4) Weight of organs: the weights of the liver, the left kidney, the left perirenal fat, the right kidney and the right perirenal fat were measured, and the coefficient of organ were calculated according to the following formula. The liver and the right kidney were weighed and stored at −80° C.

$$\text{Coefficient of organ} = \frac{\text{Weight of organs (g)}}{\text{Animal body weight on } D60 \text{ of treatment period (g)}}$$

5) Pathological test: after the end of study, the mice were fixed in a supine position, the thoracic cavities of the mice were quickly opened, normal saline was perfused throughout the whole body from the left ventricle, and then 4% paraformaldehyde was perfused for fixation. The whole artery from the heart to the lower iliac artery branch was removed, preserved in 4% paraformaldehyde fixing solution, treated and stained with Oil Red O. The aortic arch, along with the heart and common carotid artery (right) was quickly isolated and fixed with 4% paraformaldehyde. The common carotid artery was stained with Oil Red O, and the aortic arch was stained with HE and Sirius.

3.9 Statistics: The data are represented by ($\bar{x} \pm s$). The statistical analysis was carried out using SPSS 21.0 software; The pairwise comparison was conducted by one-way analysis of variance with a test level $\alpha = 0.05$.

3.10 Results 3.10.1 General clinical observation: during the study, animal #2 in the negative control group died on d30 of treatment. Anatomy showed enlarged that left kidney, with the upper half part of the left kidney being milky white and the lower half part being dark red. The left kidney was longitudinally dissected, showing a large cavity containing a milky fluid and a clear fluid. The right kidney was shriveled and atrophied, and aggregated blood clots were found.

Milky white fat-like fluid was seen in the bladder, which accumulated at the bladder outlet, accounting for about half of the intralight volume of the bladder. No visible abnormality in the gross anatomy of the rest organs of the abdominal cavity was observed, no visible abnormality in the gross anatomy of the thoracic cavity was observed, and no plaque in the thoracic aorta was observed. Judgment: In vivo cholesterol accumulation and hyperlipidemia are normal manifestations in ApoE knockout mice, and the cause of death of the mice was inferred to be individual differences, abnormal fat metabolism and excessive cholesterol accumulation. No abnormality was observed in body shape, hair, skin, feces, muscle tension, gait, spirit, respiration and the like of the animals.

3.10.2 Data in Modeling Period 3.10.2.1 Body weight in modeling period (Table 10): There was no statistical difference (p>0.05) in the body weight of animals in each group during modeling period.

3.10.2.2 Blood lipid measurements in modeling period (Table 11): Compared with the negative control group (♂), the serum TC, TG, HDL-C and LDL-C levels in the modeling group (♂) were increased (p<0.01), and the serum TC level in the modeling group (♂) was increased (p<0.05).

3.10.3 Data in Treatment Period 3.10.3.1 Body weight in treatment period (Table 12): There was no statistical difference (p>0.05) in body weight of animals between the groups in treatment period; compared with the negative control group (♂), the weight gain in the modeling control group (♂) was increased on d30 and d60 of treatment (p<0.05); compared with the modeling control group (♂), the weight gain in the positive control group (♂), the test compound 833 mg/kg group (♂) and the test compound 1667 mg/kg group (♂) was decreased on d30 and d60 of treatment (p<0.05).

3.10.3.2 Weight and coefficient of organs on d60 of treatment (Tables 13 and 14): Compared with the negative control group (♂), the weights and the coefficients of the liver and the left perirenal fat in the modeling control group (♂) were increased (p<0.05 or 0.01), the coefficients of the left kidney and the right kidney were decreased (p<0.05 or 0.01), and the weights of the left kidney and the right kidney and the coefficient of the left kidney in the modeling control group (♀) were decreased (p<0.05 or 0.01); compared with the modeling control group (♂), the weight of the left kidney in the positive control group (♂) and the test compound 833 mg/kg group (♂) was decreased (p<0.05); compared with the modeling control group (♀), the weight of the right kidney in the test compound 833 mg/kg group (♀) was decreased (p<0.05).

Figure 2:
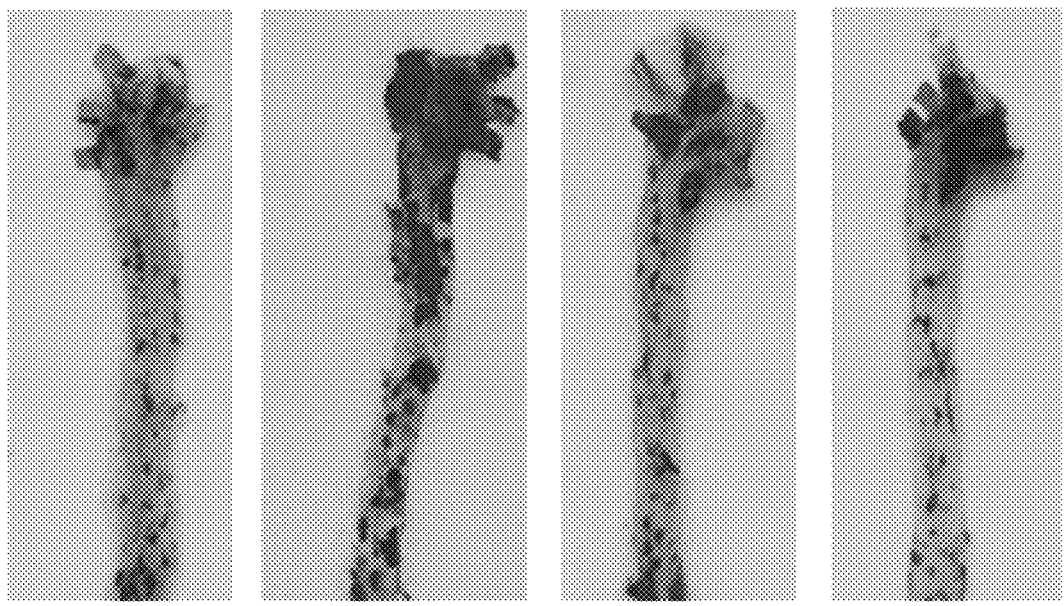
FIG. 2: comparison of effect of the traditional Chinese medicine composition disclosed herein on the formation of atherosclerotic plaques in ApoE$^{-/-}$ mice (Oil Red O-stained full-length aorta). A: a representative Oil Red O staining picture in the negative control group; B: a representative Oil Red O staining picture in the modeling control group; C: a representative Oil Red O staining picture in the traditional Chinese medicine composition 833 mg/kg group; D: a representative Oil Red O staining picture in the traditional Chinese medicine composition 1677 mg/kg group.
Figure 3:
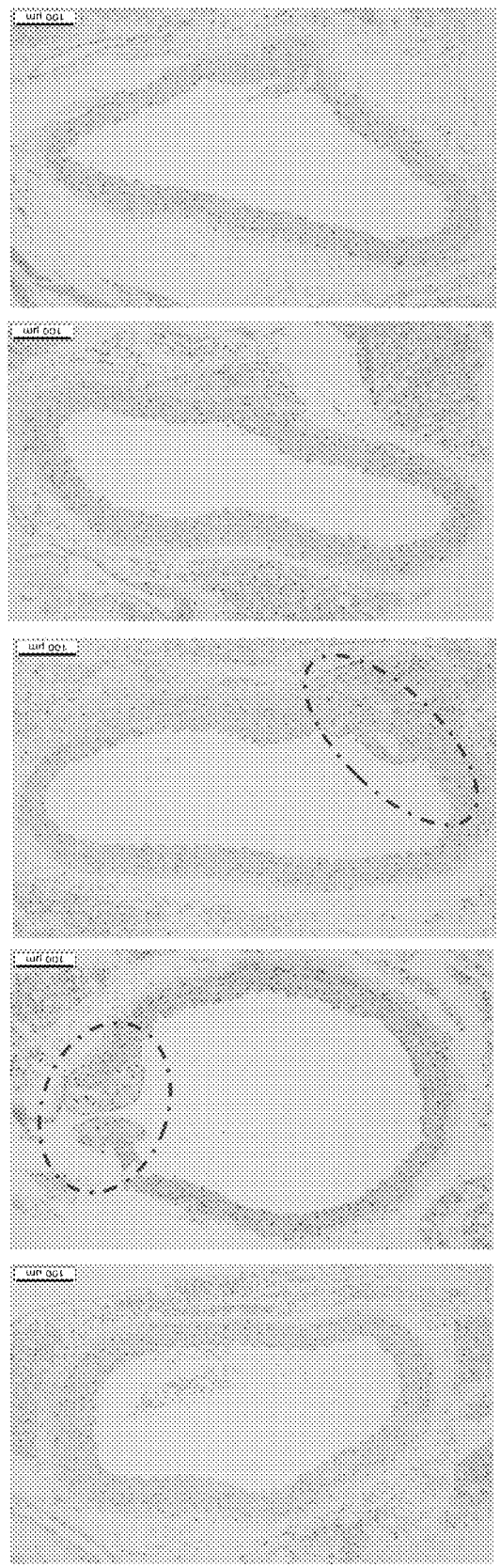
FIG. 3: comparison of effect of the traditional Chinese medicine composition disclosed herein on the formation of atherosclerotic plaques in ApoE$^{-/-}$ mice (HE-stained aortic arch section) in the negative control group, the modeling control group, the positive control group, the traditional Chinese medicine composition 833 mg/kg group and the traditional Chinese medicine composition 1677 mg/kg group.
Figure 4:
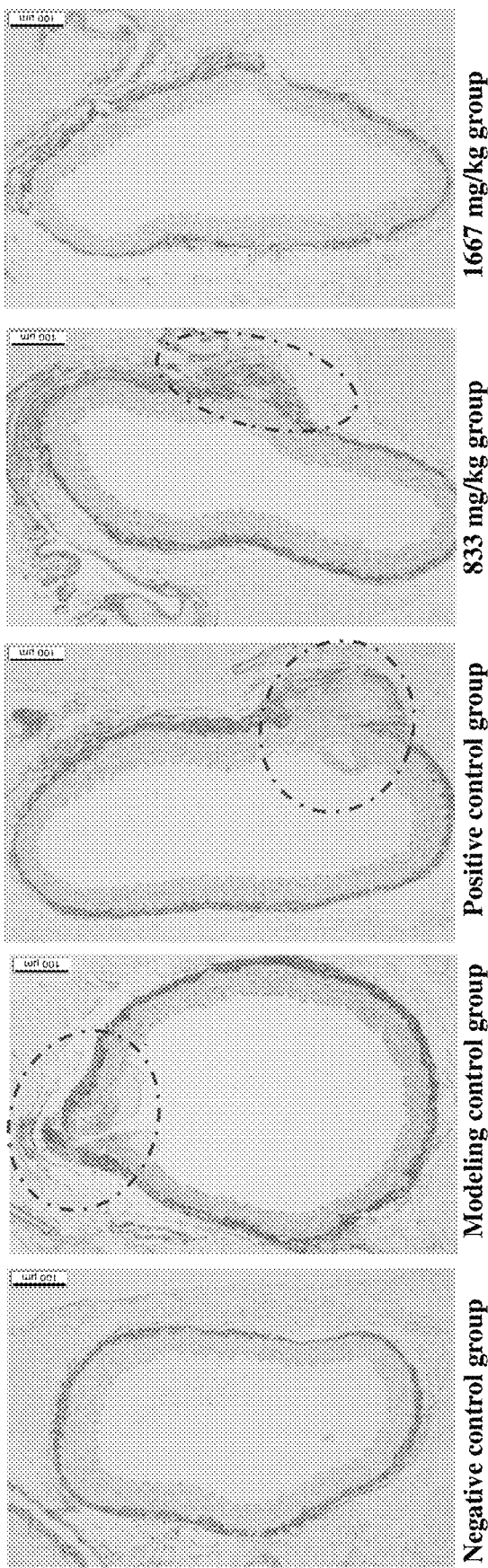
FIG. 4: comparison of effect of the traditional Chinese medicine composition disclosed herein on the formation of atherosclerotic plaques in ApoE$^{-/-}$ mice (Sirius-stained aortic arch section) in the negative control group, the modeling control group, the positive control group, the traditional Chinese medicine composition 833 mg/kg group and the traditional Chinese medicine composition 1677 mg/kg group.
Figure 5:
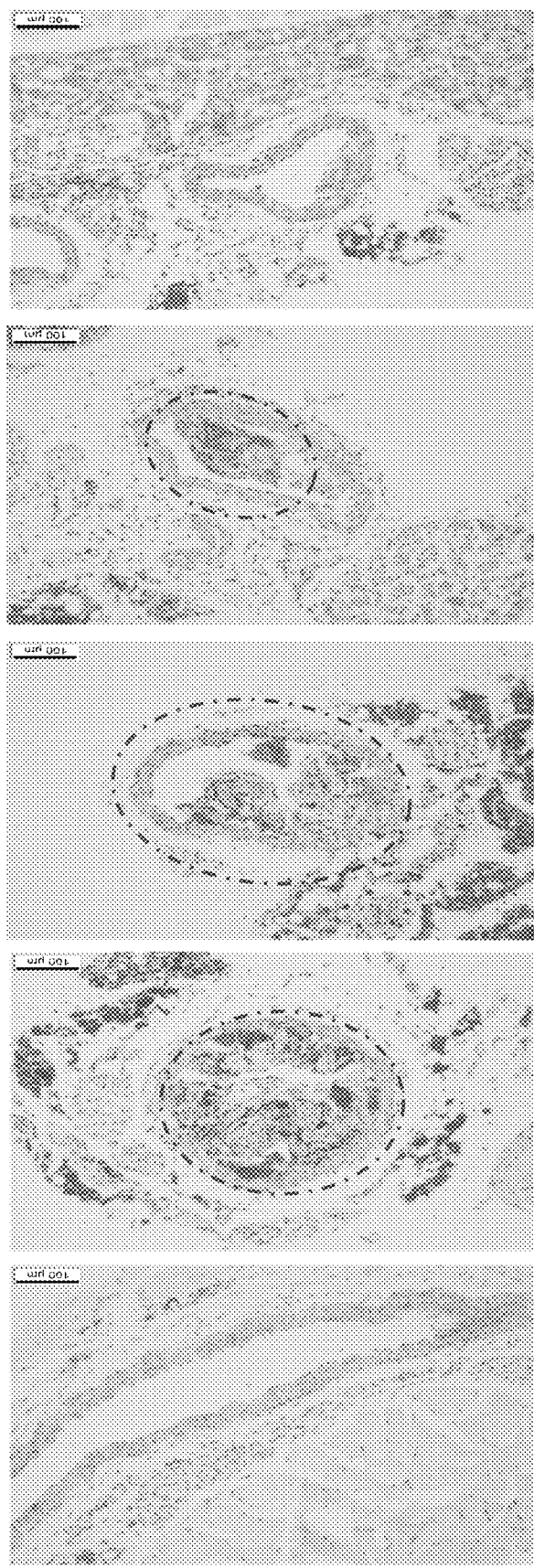
FIG. 5: comparison of effect of the traditional Chinese medicine composition disclosed herein on the formation of atherosclerotic plaques in ApoE$^{-/-}$ mice (Oil Red O-stained carotid artery section) in the negative control group, the modeling control group, the positive control group, the traditional Chinese medicine composition 833 mg/kg group and the traditional Chinese medicine composition 1677 mg/kg group.

3.10.4 Pathological examination results: The full-length aortic Oil Red O staining showed that red plaque-like substances were found in the aortic bifurcation part of ApoE$^{-/-}$ mice fed with high-fat feed, and the atherosclerotic plaque of the modeling group was significantly increased as compared to that in the negative control group (FIG. 1). Meanwhile, compared with the modeling control group, the aortic Oil Red O staining of the test compound 833 mg/kg and 1677 mg/kg groups showed that the formation of atherosclerotic plaque was obviously reduced after 60 days of treatment (FIG. 2). The HE-stained aortic arch sections showed that certain histological changes were seen in the modeling control group as compared to the negative control group, and were mainly manifested by accumulation of foam cells under the intima in the aortic arch and formation of intimal plaque (FIG. 3). The positive control group showed no significant difference as compared to the modeling control group. However, in the test compound 833 mg/kg and 1667 mg/kg groups, only foam cell aggregation was observed under the intima in the aortic arch, and no intimal plaque was formed (FIG. 3). The Sirius-stained aortic arch sections showed that the modeling control group had significant collagen fiber hyperplasia at the plaque part in the intima and the adventitia as compared to the negative control group. In the test compound groups, particularly the 1667 mg/kg group, only milder collagen fiber hyperplasia of the adventitia was found, and no collagen fiber hyperplasia was observed in the intima (FIG. 4). As shown in FIG. 5, the carotid artery Oil Red O staining showed that intraluminal red lipid droplets were formed, and the test compound 833 mg/kg and 1667 mg/kg groups were significantly superior to the modeling control group and the statin intervention group. In the test compound 1667 mg/kg group, only a trace amount of red lipid droplets were observed in the carotid lumen (FIG. 5).

TABLE 10

Body weight ($\bar{x} \pm s$, g) in modeling period

| Group | Gender | n | D1 | D8 | D15 | D22 | D29 |
|---|---|---|---|---|---|---|---|
| Negative control group | ♂ | 6 | 20.6 ± 1.5 | 22.0 ± 0.5 | 24.3 ± 0.6 | 25.3 ± 0.5 | 26.8 ± 0.6 |
| Modeling group | ♂ | 24 | 25.7 ± 1.5 | 26.2 ± 1.7 | 28.0 ± 2.1 | 28.7 ± 3.0 | 30.7 ± 2.8 |
| | ♀ | 24 | 19.1 ± 1.0 | 19.3 ± 1.3 | 20.9 ± 1.3 | 21.4 ± 1.3 | 22.2 ± 1.7 |

TABLE 11

The four blood lipid measurements ($\bar{x} \pm s$, g) in modeling period

| Group | Gender | n | TC | TG | HDL-C | LDL-C |
|---|---|---|---|---|---|---|
| Negative control group | ♂ | 6 | 20.03 ± 3.40 | 2.39 ± 0.93 | 3.16 ± 0.67 | 6.41 ± 2.07 |
| Modeling group | ♂ | 24 | 40.00 ± 4.29## | 3.91 ± 1.57## | 4.49 ± 0.62## | 23.99 ± 3.90## |
| | ♀ | 24 | 23.81 ± 1.96# | 1.59 ± 0.36 | 2.76 ± 0.28 | 11.51 ± 6.10 |

Note:
compared with the negative control group (♂), #indicates p < 0.05, and ##indicates p < 0.01

TABLE 12

Body weight data in treatment period ($\bar{x} \pm s$, g)

| Group | Gender | n | D1 | D8 | D15 | D22 | D29 | Weight gain on d30 of treatment |
|---|---|---|---|---|---|---|---|---|
| Negative control group | ♂ | 5 | 26.2 ± 0.6 | 27.5 ± 0.6 | 27.9 ± 0.9 | 28.3 ± 1.1 | 28.4 ± 2.3 | 2.1 ± 2.2 |
| Modeling control group | ♂ | 6 | 31.2 ± 3.5 | 32.2 ± 3.3 | 33.1 ± 3.8 | 33.3 ± 3.9 | 34.3 ± 3.9 | 3.2 ± 1.0# |
|  | ♀ | 6 | 22.3 ± 1.2 | 23.0 ± 1.4 | 23.4 ± 1.4 | 24.0 ± 1.9 | 24.4 ± 1.8 | 2.0 ± 1.6 |
| Positive control group | ♂ | 6 | 30.1 ± 2.8 | 30.1 ± 2.9 | 29.9 ± 2.9 | 30.4 ± 2.8 | 30.9 ± 3.7 | 0.7 ± 1.8■ |
|  | ♀ | 6 | 21.7 ± 2.4 | 22.5 ± 2.5 | 22.7 ± 2.2 | 23.2 ± 2.9 | 23.2 ± 3.1 | 1.5 ± 1.0 |
| Test compound 833 mg/kg group | ♂ | 6 | 30.2 ± 2.8 | 31.0 ± 2.9 | 30.7 ± 3.0 | 30.9 ± 3.6 | 31.8 ± 3.6 | 1.6 ± 0.9■ |
|  | ♀ | 6 | 21.1 ± 1.1 | 22.2 ± 1.1 | 22.1 ± 1.0 | 22.5 ± 0.8 | 22.9 ± 1.0 | 1.9 ± 0.7 |
| Test compound 1667 mg/kg group | ♂ | 6 | 30.6 ± 2.9 | 30.8 ± 2.7 | 31.0 ± 3.3 | 31.5 ± 3.4 | 32.2 ± 3.5 | 1.6 ± 1.0■ |
|  | ♀ | 6 | 21.2 ± 1.0 | 21.9 ± 0.8 | 22.6 ± 0.7 | 22.4 ± 0.8 | 22.7 ± 1.0 | 1.5 ± 1.5 |

| Group | Gender | n | D36 | D43 | D50 | D57 | D60 | Weight gain on d60 of treatment |
|---|---|---|---|---|---|---|---|---|
| Negative control group | ♂ | 5 | 28.5 ± 1.0 | 29.3 ± 1.2 | 30.0 ± 1.4 | 30.1 ± 1.2 | 30.4 ± 1.0 | 4.2 ± 0.8 |
| Modeling control group | ♂ | 6 | 34.7 ± 4.0 | 35.6 ± 4.2 | 36.3 ± 4.4 | 36.3 ± 4.4 | 37.4 ± 4.1 | 6.2 ± 1.5# |
|  | ♀ | 6 | 24.4 ± 2.0 | 25.1 ± 2.4 | 25.3 ± 2.6 | 25.3 ± 2.6 | 25.5 ± 2.4 | 3.2 ± 2.1 |
| Positive control group | ♂ | 6 | 30.5 ± 3.9 | 31.6 ± 4.3 | 31.8 ± 4.0 | 31.8 ± 4.0 | 32.6 ± 4.4 | 2.5 ± 2.5■ |
|  | ♀ | 6 | 23.3 ± 3.3 | 23.9 ± 4.0 | 24.2 ± 3.7 | 24.2 ± 3.7 | 24.4 ± 2.8 | 2.7 ± 0.7 |
| Test compound 833 mg/kg group | ♂ | 6 | 32.1 ± 3.8 | 33.0 ± 4.0 | 33.4 ± 4.0 | 33.9 ± 3.8 | 34.2 ± 4.1 | 4.1 ± 1.7■ |
|  | ♀ | 6 | 22.8 ± 0.8 | 25.3 ± 4.8 | 23.5 ± 1.1 | 24.1 ± 0.8 | 24.2 ± 0.7 | 3.1 ± 0.9 |
| Test compound 1667 mg/kg group | ♂ | 6 | 32.0 ± 3.6 | 32.9 ± 3.7 | 33.5 ± 3.9 | 34.2 ± 4.0 | 34.0 ± 4.1 | 3.4 ± 1.3■ |
|  | ♀ | 6 | 22.7 ± 1.1 | 23.5 ± 1.1 | 23.8 ± 1.5 | 24.0 ± 1.4 | 24.1 ± 1.9 | 2.9 ± 2.8 |

Note: compared with the negative control group (♂), #indicates $p < 0.05$; compared with the modeling control group (♂), ■indicates $p < 0.05$.

TABLE 13

Weight of organs on d60 of treatment ($\bar{x} \pm s$)

| | | | Weight of organs (g) | | | | |
|---|---|---|---|---|---|---|---|
| Group | Gender | n | Liver | Left kidney ($10^{-1}$) | Right kidney ($10^{-1}$) | Left perirenal fat ($10^{-1}$) | Right perirenal fat ($10^{-1}$) |
| Negative control group | ♂ | 5 | 1.31 ± 0.07 | 1.76 ± 0.09 | 1.85 ± 0.19 | 2.86 ± 3.40 | 1.18 ± 0.45 |
| Modeling control group | ♂ | 6 | 1.83 ± 0.28## | 1.90 ± 0.13 | 1.86 ± 0.18 | 3.85 ± 1.10 | 3.54 ± 0.93## |
|  | ♀ | 6 | 1.17 ± 0.15 | 1.31 ± 0.23## | 1.42 ± 0.09## | 1.13 ± 0.61 | 1.09 ± 0.57 |
| Positive control group | ♂ | 6 | 1.56 ± 0.28 | 1.67 ± 0.19■ | 1.79 ± 0.18 | 2.54 ± 1.27 | 2.67 ± 1.37 |
|  | ♀ | 6 | 1.05 ± 0.17 | 1.26 ± 0.18 | 1.32 ± 0.18 | 1.10 ± 0.89 | 0.89 ± 0.66 |
| Test compound 833 mg/kg group | ♂ | 6 | 1.56 ± 0.41 | 1.77 ± 0.07■ | 1.87 ± 0.16 | 2.83 ± 1.51 | 2.72 ± 1.40 |
|  | ♀ | 6 | 1.03 ± 0.03 | 1.27 ± 0.06 | 1.27 ± 0.07* | 0.81 ± 0.22 | 0.69 ± 0.23 |
| Test compound 1667 mg/kg group | ♂ | 6 | 1.32 ± 0.52 | 1.76 ± 0.21 | 1.84 ± 0.17 | 2.99 ± 1.28 | 2.96 ± 1.41 |
|  | ♀ | 6 | 1.06 ± 0.04 | 1.30 ± 0.06 | 1.35 ± 0.05 | 0.95 ± 0.63 | 0.78 ± 0.53 |

Note: compared with the negative control group (♂), #indicates $p < 0.05$, and ##indicates $p < 0.01$; compared with the modeling control group (♂), ■indicates $p < 0.05$; compared with the modeling control group (♀), *indicates $p < 0.05$.

TABLE 14

Coefficient of organs on d60 of treatment ($\bar{x} \pm s$)

| | | | Coefficient of organs | | | | |
|---|---|---|---|---|---|---|---|
| Group | Gender | n | Liver | Left kidney ($10^{-1}$) | Right kidney ($10^{-1}$) | Left perirenal fat ($10^{-1}$) | Right perirenal fat ($10^{-1}$) |
| Negative control group | ♂ | 5 | 4.30 ± 0.20 | 5.80 ± 0.28 | 6.09 ± 0.67 | 9.42 ± 11.22 | 3.87 ± 1.35 |
| Modeling control group | ♂ | 6 | 4.88 ± 0.39# | 5.13 ± 0.49# | 4.99 ± 0.28## | 10.17 ± 1.86 | 9.37 ± 1.40## |
|  | ♀ | 6 | 4.56 ± 0.23 | 5.12 ± 0.61# | 5.58 ± 0.40 | 4.30 ± 1.89 | 4.21 ± 2.05 |
| Positive control group | ♂ | 6 | 4.77 ± 0.35 | 5.16 ± 0.59 | 5.51 ± 0.52 | 7.43 ± 3.22 | 7.81 ± 3.49 |
|  | ♀ | 6 | 4.28 ± 0.29 | 5.14 ± 0.19 | 5.42 ± 0.34 | 4.30 ± 2.80 | 3.45 ± 2.03 |
| Test compound | ♂ | 6 | 4.51 ± 0.78 | 5.20 ± 0.46 | 5.51 ± 0.53 | 7.99 ± 3.33 | 7.69 ± 3.05 |

TABLE 14-continued

Coefficient of organs on d60 of treatment ($\bar{x} \pm s$)

| | | | | Coefficient of organs | | | |
|---|---|---|---|---|---|---|---|
| Group | Gender | n | Liver | Left kidney ($10^{-1}$) | Right kidney ($10^{-1}$) | Left perirenal fat ($10^{-1}$) | Right perirenal fat ($10^{-1}$) |
| 833 mg/kg group | ♀ | 6 | 4.27 ± 0.24 | 5.26 ± 0.28 | 5.25 ± 0.31 | 3.36 ± 0.90 | 2.88 ± 0.97 |
| Test compound | ♂ | 6 | 3.87 ± 1.32 | 5.24 ± 0.84 | 5.46 ± 0.58 | 8.57 ± 2.52 | 8.45 ± 2.89 |
| 1667 mg/kg group | ♀ | 6 | 4.43 ± 0.32 | 5.40 ± 0.30 | 5.61 ± 0.44 | 3.83 ± 2.10 | 3.17 ± 1.84 |

Note:
compared with the negative control group (♂), #indicates $p < 0.05$, and ##indicates $p < 0.01$; compared with the modeling control group (♂), ■indicates $p < 0.05$; compared with the modeling control group (♀), *indicates $p < 0.05$.

3.11 Summary

The traditional Chinese medicine composition disclosed herein has significant effects on reducing the formation of atherosclerotic plaques and reducing the weight gain in model animals.

Example 4. Clinical Trials for Treatment of Hyperlipidemia

The subjects were from Zhejiang Huzhou Ruibo Traditional Chinese Medicine Clinic (No. 322, Meizhou Road, Huzhou City, Zhejiang Province) and Beijing Tongyitang Clinic (1st Floor, Building 4, Zhongguancun Life Science Park, Changping District, Beijing).

Data of treatment using the powder A, B or C for dry ointment extract of the present invention in these subjects from the two clinics as described above were collected, where 14 subjects had increased total cholesterol (>6.2 mmol/L) and triglyceride (>1.7 mmol/L), 11 subjects had increased total cholesterol, and 88 subjects had increased triglyceride (Table 15).

The patients received one to three 14-day courses of treatment. The patients were administered twice daily, receiving 1 or 2 bags of granule formulation each time according to disease conditions, each bag of granule formulation containing 1250 mg of the powder A, B or C for dry ointment extract.

Figure 6:
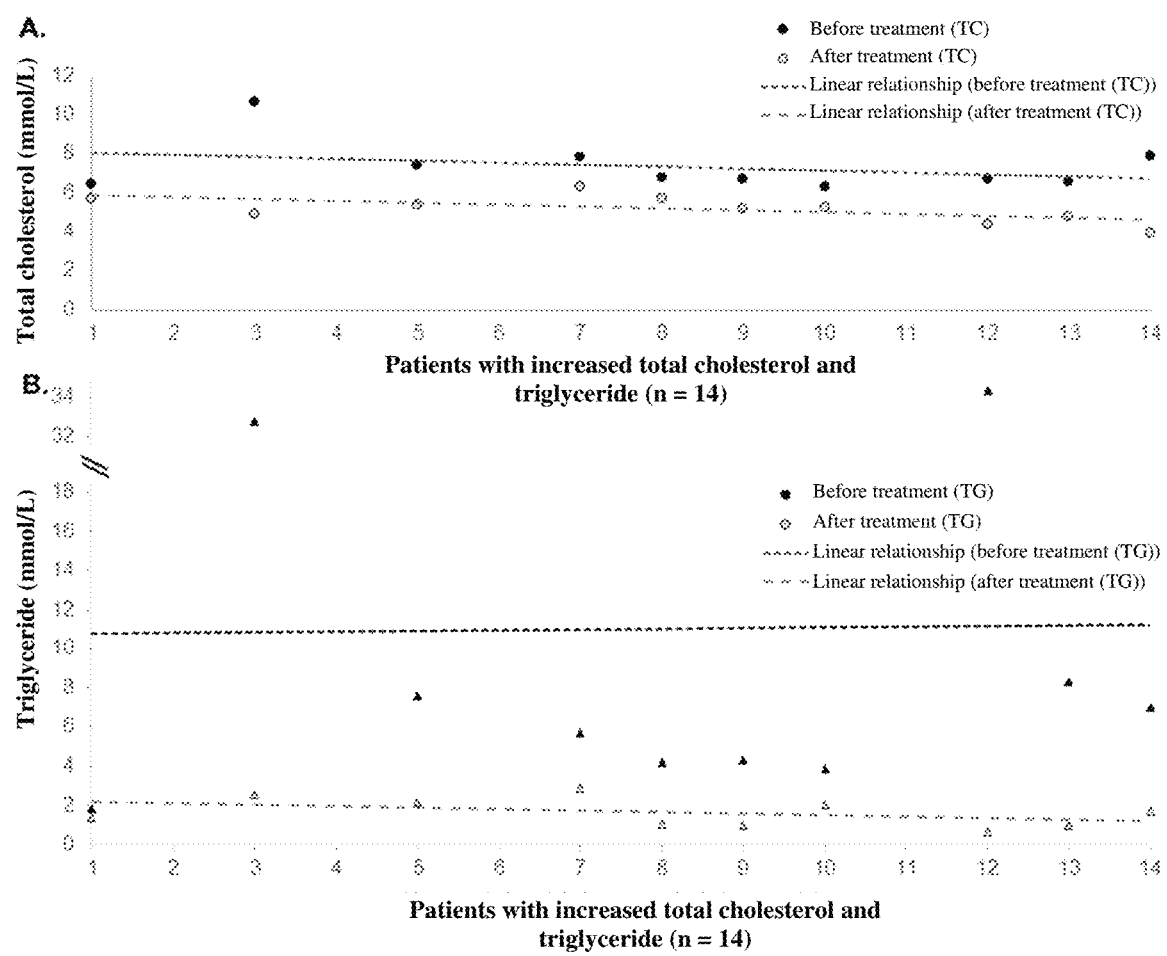
FIG. 6: the treatment outcome of the traditional Chinese medicine composition disclosed herein in 14 patients with increased total cholesterol and increased triglyceride. A: analysis of total cholesterol before and after treatment; B: analysis of triglyceride before and after treatment.

With 10% reduction in total cholesterol or triglyceride levels as the efficacy endpoint, in the 14 subjects with increased total cholesterol and triglyceride, nearly 79% of the patients had effective reduction in total cholesterol, 93% of the patients had effective reduction in triglyceride, and 10 patients had both effective reductions (Table 15 and FIG. 6).

Figure 7:
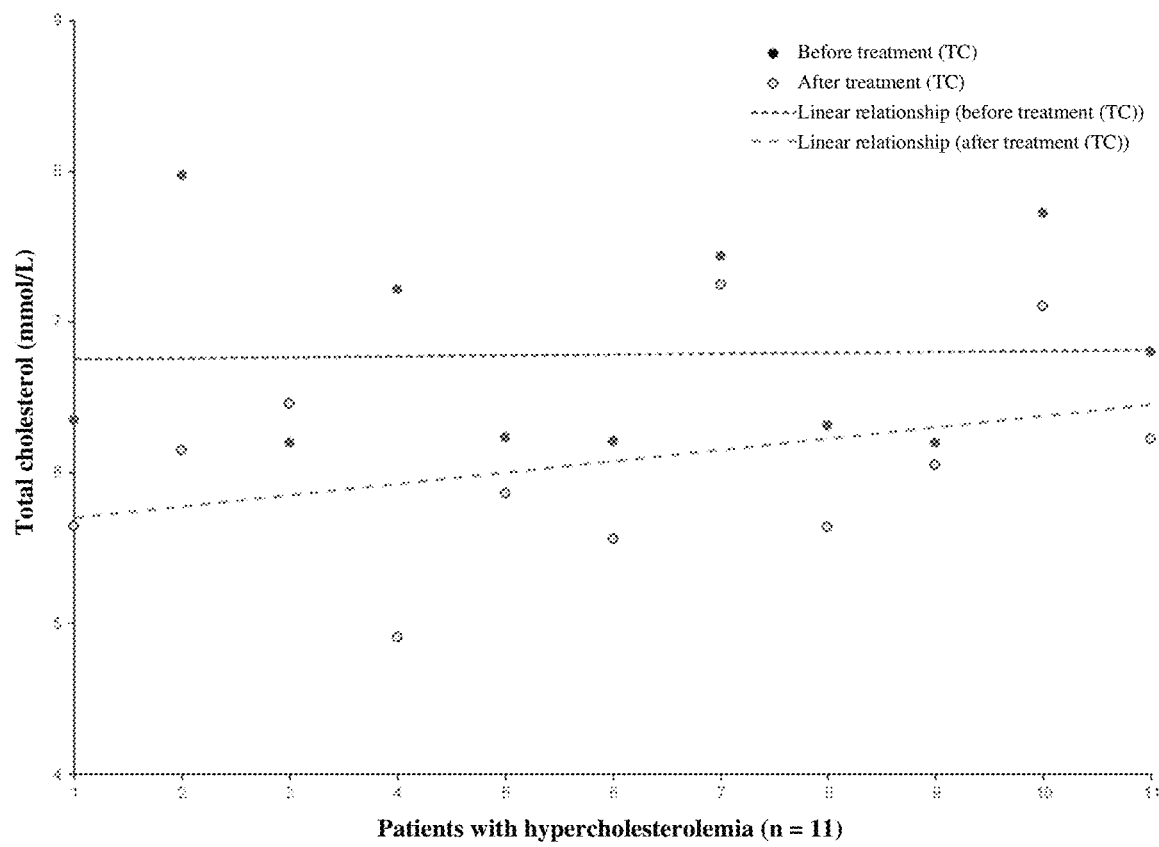
FIG. 7: the treatment outcome of the traditional Chinese medicine composition disclosed herein in 11 patients with hypercholesterolemia and analysis of total cholesterol before and after treatment.
Figure 8:
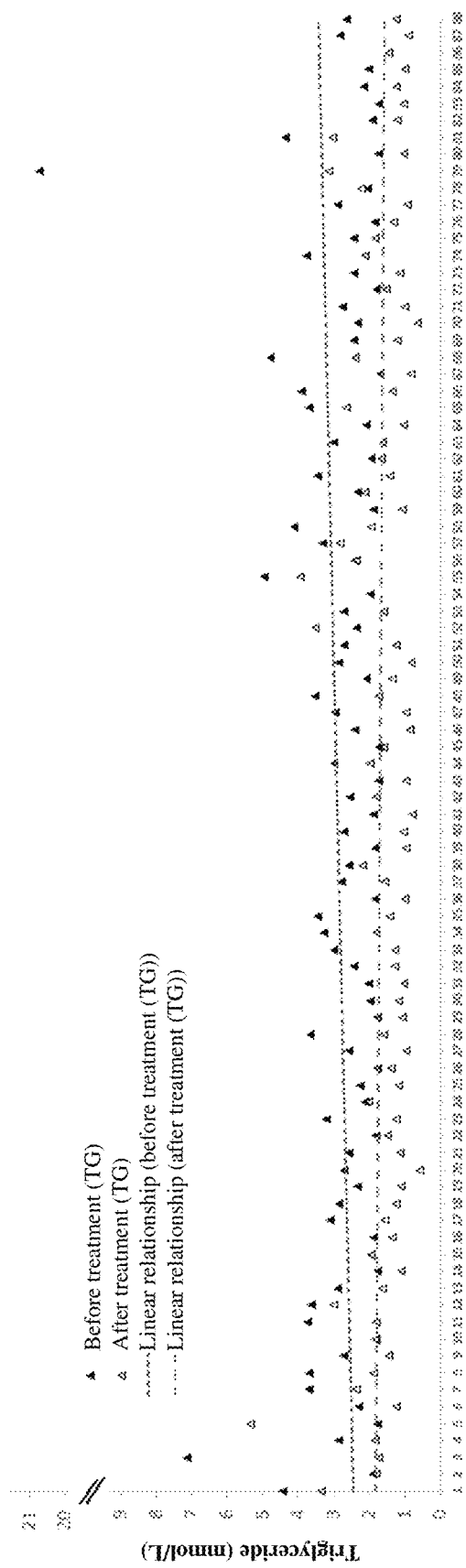
FIG. 8: the treatment outcome of the traditional Chinese medicine composition disclosed herein in 88 patients with hypertriglyceridemia and analysis of triglyceride before and after treatment.

The traditional Chinese medicine composition disclosed herein has an effective rate of 45% in reducing increased total cholesterol (shown in Table 15 and FIG. 7) and an effective rate of close to 90% in reducing hypertriglyceridemia (shown in Table 15 and FIG. 8). The traditional Chinese medicine composition disclosed herein has excellent efficacy on patients with severe hyperlipidemia, particularly in subjects with severe blood triglyceride (triglyceride>5.6 mmol/L).

TABLE 15

Summary of blood total cholesterol and triglyceride before and after treatment in 113 subjects with hyperlipidemia

| | Number of subjects | medicines (number) | Total cholesterol (TC > 6.2 mmol/L) | | | Triglyceride (TG > 1.7 mmol/L) | | |
|---|---|---|---|---|---|---|---|---|
| | | | Before treatment (Avg. ± Std., mmol/L) | After treatment (Avg. ± Std., mmol/L) | Ratio of 10% decrease or more | Before treatment (Avg. ± Std., mmol/L) | After treatment (Avg. ± Std., mmol/L) | Ratio of 10% decrease or more |
| Patients with hypercholesterolemia (TC) | 11 | A(3), C(8) | 6.78 ± 0.68 | 6.08 ± 0.68▲ | 45.0% | | | |
| Patients with hypertriglyceridemia (TG) | 88 | A(71), B(17) | | | | 2.95 ± 2.19 | 1.69 ± 1.07▲▲ | 88.7% |
| Patients with hyperlipemia (increased TC and TG) | 14 | A(7), B(4), C(3) | 7.18 ± 1.14 | 5.8 ± 1.59▲▲ | 78.6% | 8.67 ± 10.73 | 1.54 ± 0.75▲▲ | 92.8% |

Note:
compared between groups, independent sample T test; "▲"indicates $P < 0.05$, and "▲▲"indicates $P < 0.01$

Example 5. Typical Cases of Hyperlipidemia Treatment

Example 5-1

Shao, male, visited the doctor in Zhejiang Huzhou Ruibo Traditional Chinese Medicine Clinic (No. 322, Meizhou Road, Huzhou City, Zhejiang Province) in 2016. The diagnosis indicated that the blood was milky white, the blood triglyceride was 33.4 mmol/L, and the blood total cholesterol was 6.71 mmol/L. The granule formulation was administered twice daily with 2 bags each time, each bag containing 1250 mg of the powder A for dry ointment extract. After one course of treatment (14 days), triglyceride was reduced to 0.62 mmol/L, and total cholesterol was reduced to 4.41 mmol/L, which both returned to the normal levels.

Example 5-2

Chen, female, visited the doctor in Zhejiang Huzhou Ruibo Traditional Chinese Medicine Clinic (No. 322, Meizhou Road, Huzhou City, Zhejiang Province) in 2016. Chen had long-term use of statin lipid-lowering agent at visiting, and the diagnosis indicated that the blood triglyceride was 8.31 mmol/L and the total cholesterol was 6.59 mmol/L, which were both higher than normal values. Especially, the blood triglyceride was much higher than normal level. The granule formulation was administered twice daily with 2 bags each time, each bag containing 1250 mg of the powder A for dry ointment extract. After one course of treatment (14 days), triglyceride was reduced to 1.01 mmol/L, and total cholesterol was reduced to 4.77 mmol/L, which both returned to the normal levels.

Example 5-3

Huang, male, visited the doctor in Zhejiang Huzhou Ruibo Traditional Chinese Medicine Clinic (No. 322, Meizhou Road, Huzhou City, Zhejiang Province) in 2017. When Dai visited the doctor, the diagnosis indicated that the blood triglyceride was 8.05 mmol/L and the total cholesterol was 5.51 mmol/L, which were both higher than normal values. Especially, the triglyceride was increased. The granule formulation was administered twice daily with 1 bags each time, each bag containing 1250 mg of the powder B for dry ointment extract. After two courses of treatment, the triglyceride was reduced to 1.45 mmol/L and returned to normal level.

Example 5-4

Yu, male, visited the doctor in Zhejiang Huzhou Ruibo Traditional Chinese Medicine Clinic (No. 322, Meizhou Road, Huzhou City, Zhejiang Province) in 2018. When Chen visited the doctor, the diagnosis indicates that the blood triglyceride was 7.13 mmol/L and the total cholesterol was 4.51 mmol/L, suggesting hypertriglyceridemia. The granule formulation was administered twice daily with 1 bags each time, each bag containing 1250 mg of the powder B for dry ointment extract. After two courses of treatment, triglyceride was reduced to 1.75 mmol/L and returned to normal level. The total cholesterol had no changes.

Example 5-5

Shen, male, visited the doctor in Zhejiang Huzhou Ruibo Traditional Chinese Medicine Clinic (No. 322, Meizhou Road, Huzhou City, Zhejiang Province) in 2017. When Xu visited the doctor, the diagnosis indicated that the blood triglyceride was 0.95 mmol/L and the total cholesterol was 7.22 mmol/L, suggesting hypercholesterolemia. The granule formulation was administered twice daily with 1 bags each time, each bag containing 1250 mg of the powder C for dry ointment extract. After three courses of treatment, total cholesterol was reduced to 4.91 mmol/L within the normal level. The triglycerides had no significant changes.

Example 6. Typical Cases of Atherosclerosis Treatment

Example 6-1

Yang, male, visited the doctor in Beijing Tongyitang Clinic (1st Floor, Building 4, Zhongguancun Life Science Park, Changping District, Beijing) in 2019. At visiting, the diagnosis indicated that arteriosclerotic plaques were formed in the bilateral common carotid artery and the right clavicle, and multiple plaques were formed in the right common carotid artery, with the largest one having a length of 16.5 mm and a thickness of 3.9 mm; meanwhile, arteriosclerotic plaques were formed in the right clavicle. A plurality of plaques were formed on the left common carotid artery, with a maximum length of 3.5 mm and a thickness of 1.6 mm; the diameter of the right vertebral artery was 2.8 mm, the average blood flow rate was 0.21 m/s, and the blood flow volume was 77 mL/min.

The granule formulation was administered twice daily with 2 bags each time, each bag containing 1250 mg of the powder A for dry ointment extract. After eight courses of treatment and four months of treatment, the sclerosis plaque in the right common carotid artery became small and disappeared, with the largest one having a length of 10.0 mm and a thickness of 1.8 mm. The arteriosclerosis plaque in the right clavicle upper disappeared, the diameter of the vertebral artery increased (3.2 mm), the blood flow rate (0.21 m/s) and the blood flow volume were significantly improved (to 135 mL/min after treatment for the blood flow volume).

Example 6-2

Wang, male, 40 years old, visited the doctor in Beijing Tongyitang Clinic (1st Floor, Building 4, Zhongguancun Life Science Park, Changping District, Beijing) in 2018. When he visited the doctor, the diagnosis indicated that arteriosclerotic plaques of about 1.6 mm were formed in the bilateral common carotid artery.

The granule formulation was administered twice daily with 2 bags each time, each bag containing 1250 mg of the powder A for dry ointment extract. After six courses of treatment (3 months of treatment), no obvious plaque was formed in the left and right common carotid arteries, and the original sclerotic plaques disappeared.

The invention claimed is:

1. An oral formulation for preventing or treating increased blood lipids, increased triglyceride, increased cholesterol, hyperlipidemia and atherosclerosis wherein the oral formulation is prepared by decocting and/or extracting the following raw materials in part by weight: 20-30 parts of thorowax root, 10-20 parts of immature orange fruit, 5-15 parts of raw rhubarb, 5-10 parts of baical skullcap root, 5-15 parts of white peony root, 5-10 parts of dried ginger, 7-15 parts of leech, 5-15 parts of liquorice root, 5-15 parts of tangshen, 5-15 parts of largehead *atractylodes* rhizome and 10-20 parts of *pinellia tuber*, and wherein the oral formulation is in oral dosage form selected from the group consisting of a tablet, a sugar-coated tablet, a film-coated tablet, an enteric-coated tablet, a capsule, a hard capsule, a soft capsule, a lozenge, a granule, a pill, a suspension, a pellet, and an ointment.

2. The oral formulation according to claim 1, wherein the oral formulation is prepared by decocting and/or extracting the following raw materials in part by weight: 25 parts of thorowax root, 15 parts of immature orange fruit, 10 parts of raw rhubarb, 6 parts of baical skullcap root, 10 parts of white peony root, 6 parts of dried ginger, 10 parts of leech, 10 parts of liquorice root, 10 parts of tangshen, 10 parts of largehead *atractylodes* rhizome and 15 parts of *pinellia tuber*.

3. An oral formulation for preventing or treating increased blood lipids, increased triglyceride, increased cholesterol, hyperlipidemia and atherosclerosis wherein the oral formulation is prepared by decocting and/or extracting the following raw materials in part by weight: 20-30 parts of thorowax root, 10-20 parts of immature orange fruit, 5-15 parts of raw rhubarb, 5-10 parts of baical skullcap root, 5-15 parts of white peony root, 5-10 parts of dried ginger, 7-15 parts of leech, 5-15 parts of liquorice root, 5-15 parts of tangshen, 5-15 parts of largehead *atractylodes* rhizome, 10-20 parts of *pinellia tuber* and 10-35 parts of oyster shell, and wherein the oral formulation is in oral dosage form selected from the group consisting of a tablet, a sugar-coated tablet, a film-coated tablet, an enteric-coated tablet, a capsule, a hard capsule, a soft capsule, a lozenge, a granule, a pill, a suspension, a pellet, and an ointment.

4. The oral formulation according to claim 3, wherein the oral formulation is prepared by decocting and/or extracting the following raw materials in part by weight: 25 parts of thorowax root, 15 parts of immature orange fruit, 10 parts of raw rhubarb, 6 parts of baical skullcap root, 10 parts of white peony root, 6 parts of dried ginger, 10 parts of leech, 10 parts of liquorice root, 10 parts of tangshen, 10 parts of largehead *atractylodes* rhizome, 15 parts of *pinellia tuber* and 30 parts of oyster shell.

5. An oral formulation for preventing or treating increased blood lipids, increased triglyceride, increased cholesterol, hyperlipidemia and atherosclerosis wherein the oral formulation is prepared by decocting and/or extracting the following raw materials in part by weight: 20-30 parts of thorowax root, 10-20 parts of immature orange fruit, 5-15 parts of raw rhubarb, 5-10 parts of baical skullcap root, 5-15 parts of white peony root, 5-10 parts of dried ginger, 7-15 parts of leech, 5-15 parts of liquorice root, 5-15 parts of tangshen, 5-15 parts of largehead *atractylodes* rhizome, 10-20 parts of *pinellia tuber*, 10-35 parts of oyster shell and 5-12 parts of red yeast rice, and wherein the oral formulation is in oral dosage form selected from the group consisting of a tablet, a sugar-coated tablet, a film-coated tablet, an enteric-coated tablet, a capsule, a hard capsule, a soft capsule, a lozenge, a granule, a pill, a suspension, a pellet, and an ointment.

6. The formulation according to claim 5, wherein the formulation is prepared by decocting and/or extracting the following raw materials in part by weight: 25 parts of thorowax root, 15 parts of immature orange fruit, 10 parts of raw rhubarb, 6 parts of baical skullcap root, 10 parts of white peony root, 6 parts of dried ginger, 10 parts of leech, 10 parts of liquorice root, 10 parts of tangshen, 10 parts of largehead *atractylodes* rhizome, 15 parts of *pinellia tuber*, 30 parts of oyster shell and 10 parts of red yeast rice.

7. The oral formulation according to claim 1, wherein the oral dosage form is selected from the group consisting of a tablet, a sugar-coated tablet, a film-coated tablet, an enteric-coated tablet, a capsule, a hard capsule, a soft capsule, and a lozenge.

8. The oral formulation according to claim 3, wherein the oral dosage form is selected from the group consisting of a tablet, a sugar-coated tablet, a film-coated tablet, an enteric-coated tablet, a capsule, a hard capsule, a soft capsule, and a lozenge.

9. The oral formulation according to claim 5, wherein the oral dosage form is selected from the group consisting of a tablet, a sugar-coated tablet, a film-coated tablet, an enteric-coated tablet, a capsule, a hard capsule, a soft capsule, and a lozenge.

\* \* \* \* \*